(12) United States Patent
Hantash

(10) Patent No.: US 10,502,738 B2
(45) Date of Patent: *Dec. 10, 2019

(54) HLA G-MODIFIED CELLS AND METHODS

(71) Applicant: AgeX Therapeutics, Inc., Alameda, CA (US)

(72) Inventor: Basil M. Hantash, East Palo Alto, CA (US)

(73) Assignee: AGEX THERAPEUTICS, INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,964

(22) Filed: Jun. 16, 2017

(65) Prior Publication Data

US 2017/0292952 A1 Oct. 12, 2017

Related U.S. Application Data

(63) Continuation of application No. 14/608,004, filed on Jan. 28, 2015, now Pat. No. 9,714,280, which is a continuation of application No. PCT/US2013/052767, filed on Jul. 30, 2013.

(60) Provisional application No. 61/677,739, filed on Jul. 31, 2012.

(51) Int. Cl.

| | |
|---|---|
| *C12N 5/00* | (2006.01) |
| *C12N 5/071* | (2010.01) |
| *C07K 14/74* | (2006.01) |
| *A01K 67/027* | (2006.01) |
| *G01N 33/569* | (2006.01) |
| *C12N 5/073* | (2010.01) |
| *C07K 16/28* | (2006.01) |
| *G01N 33/566* | (2006.01) |
| *G01N 33/68* | (2006.01) |
| *A61K 35/12* | (2015.01) |
| *A61K 35/28* | (2015.01) |
| *A61K 35/33* | (2015.01) |
| *A61K 35/407* | (2015.01) |
| *A61K 35/44* | (2015.01) |

(52) U.S. Cl.

CPC ... *G01N 33/56977* (2013.01); *A01K 67/0271* (2013.01); *A61K 35/12* (2013.01); *A61K 35/28* (2013.01); *A61K 35/33* (2013.01); *A61K 35/407* (2013.01); *A61K 35/44* (2013.01); *C07K 14/70539* (2013.01); *C07K 16/28* (2013.01); *C12N 5/0603* (2013.01); *G01N 33/566* (2013.01); *G01N 33/6893* (2013.01); *A01K 2207/12* (2013.01); *A01K 2227/105* (2013.01); *A01K 2267/025* (2013.01); *C12N 2510/00* (2013.01); *G01N 2333/705* (2013.01); *G01N 2333/71* (2013.01); *G01N 2800/245* (2013.01)

(58) Field of Classification Search
USPC ........................................ 435/366, 325, 372
See application file for complete search history.

(56) References Cited

U.S. PATENT DOCUMENTS

| | | | |
|---|---|---|---|
| 5,449,614 A | 9/1995 | Danos et al. | |
| 5,464,764 A | 11/1995 | Capecchi et al. | |
| 5,650,135 A | 7/1997 | Contag et al. | |
| 5,741,657 A | 4/1998 | Tsien et al. | |
| 5,744,320 A | 4/1998 | Sherf et al. | |
| 6,031,094 A | 2/2000 | Tsien et al. | |
| 6,200,806 B1 | 3/2001 | Thomson | |
| 6,333,195 B1 | 12/2001 | Respess et al. | |
| 6,982,431 B2 | 1/2006 | Modlin et al. | |
| 7,217,569 B2 | 5/2007 | Thomson | |
| 7,238,842 B2 | 7/2007 | Wood et al. | |
| 7,264,968 B2 | 9/2007 | Melton et al. | |
| 7,332,332 B2 | 2/2008 | Riemen et al. | |
| 7,763,466 B2 | 7/2010 | Keller et al. | |
| 7,955,849 B2 | 6/2011 | Keller et al. | |
| 7,960,166 B2 | 6/2011 | Vacanti et al. | |
| 8,003,389 B2 | 8/2011 | Riemen et al. | |
| 8,039,259 B2 | 10/2011 | Riemen et al. | |
| 8,048,675 B1 | 11/2011 | Irion | |
| 8,048,999 B2 | 11/2011 | Yamanaka et al. | |
| 8,058,065 B2 | 11/2011 | Yamanaka et al. | |
| 8,192,990 B2 | 6/2012 | Riemen et al. | |

(Continued)

FOREIGN PATENT DOCUMENTS

| | | |
|---|---|---|
| EP | 2880054 B1 | 1/2019 |
| WO | WO-95/10619 A2 | 4/1995 |

(Continued)

OTHER PUBLICATIONS

Paul, P., et al., "HLA-G, -E, -F Preworkshop: Tools and Protocols for Analysis of Non-Classical Class I Genes Transcription and Protein Expression", Human Immunology, 61:1177-1195, 2000 (19 pages).

(Continued)

*Primary Examiner* — Maria G Leavitt
(74) *Attorney, Agent, or Firm* — Wilmer Cutler Pickering Hale and Dorr LLP

(57) ABSTRACT

Disclosed herein are methods for producing genetically modified cells expressing HLA-G (e.g., cell surface HLA-G) persistently, and nucleic acid compositions useful for generating such genetically modified cells. Also disclosed are cell therapy methods that utilize genetically modified cells that express HLA-G persistently. The HLA-G genetic modifications described herein provide the cells with characteristics of reduced immunogenicity and/or improved immunosuppression, such that these cells have the promise of being universal or improved donor cells for transplants, cellular and tissue regeneration or reconstruction, and other therapies.

13 Claims, 22 Drawing Sheets

Specification includes a Sequence Listing.

(56) References Cited

U.S. PATENT DOCUMENTS

| | | |
|---|---|---|
| 8,592,211 B2 | 11/2013 | Brivanlou et al. |
| 8,617,810 B2 | 12/2013 | Heller et al. |
| 8,647,871 B2 | 2/2014 | Hantash |
| 2006/0141577 A1 | 6/2006 | Otte et al. |
| 2007/0036773 A1 | 2/2007 | Cooper et al. |
| 2007/0134761 A1 | 6/2007 | Chatellard et al. |
| 2007/0184513 A1 | 8/2007 | Tsien et al. |
| 2008/0026407 A1 | 1/2008 | Wood et al. |
| 2008/0145882 A1 | 6/2008 | Darzins et al. |
| 2008/0248005 A1 | 10/2008 | Phan |
| 2009/0156532 A1 | 6/2009 | Ober et al. |
| 2010/0055785 A1 | 3/2010 | Hantash |

FOREIGN PATENT DOCUMENTS

| | | |
|---|---|---|
| WO | WO-2006048459 A2 | 5/2006 |
| WO | WO-2007/091078 A2 | 8/2007 |
| WO | WO-2008121894 A2 | 10/2008 |

OTHER PUBLICATIONS

Communication from European Patent Office dated Jul. 14, 2017 in related European Patent Application No. 13825511.2 (10 pages).
Ausubel, F. M., et al., "Current Protocols in Molecular Biology: Chapter 9," John Wiley & Sons, Inc., New York, 201 pages (2003).
Braam, S. R., et al., "Improved genetic manipulation of human embryonic stem cells," Nature Methods, vol. 5, pp. 389-392, 23 pages (Jun. 2008).
Burns, C. J., et al., "Diabetes mellitus: a potential target for stem cell therapy," Curr. Stem Cell Res. Ther., vol. 1, No. 2, pp. 255-266 (May 2006).
Chan, et al., "Generation of High-Level Stable ransgene Expressing Human Embryonic Stem Cell Lines Using Chinese Hamster Elongation Factor-1 α Promoter Systems", Stem Cells and Development, 17:825-836, 2008.
Chen, C. P., et al., "From Stem Cells to Oligodendrocytes: Prospects for Brain Therapy," Stem Cell Reviews, vol. 3, No. 4, pp. 280-288 (Dec. 2007).
Coutts, M. and Keirstead, H. S., "Stem cells for the treatment of spinal cord injury," Exp. Neurol., vol. 209, No. 2, pp. 368-377 (Feb. 2008).
Donadi, E. A., et al., "Implications of the polymorphism of HLC-G on its function, regulatioin, evolution and disease association", Cell. Mol. Life Sci., 68:369-395, 2011 (27 pages).
Geraghty, D. E., et al., "A human major histocompatibility complex class I gene that encodes a protein with a shortened cytoplasmic segment," Proc. Natl. Acad. Sci. USA, vol. 84, pp. 9145-9149 (Dec. 1987).
Goswami, J. and Rao, M., "Embryonic stem cell therapy," IDrugs, vol. 10, No. 10, pp. 713-719 (2007).
Hasegawa, K., et al., "Efficient Multicistronic Expression of a Transgene in Human Embryonic Stem Cells," Stem Cells, vol. 25, pp. 1707-1712 (2007).
Heiskanen, A., et al., "N-glycolylneuraminic acid xenoantigen contamination of human embryonic and mesenchymal stem cells is substantially reversible," Stem Cells, vol. 25, No. 1, pp. 197-202 (Jan. 2007).
International Search Report and Written Opinion issued by the U.S. Patent and Trademark Office as International Searching Authority for International Application No. PCT/US2013/052767 dated Feb. 6, 2014 (12 pages).
Janssens, S., et al., "Autologous bone marrow-derived stem-cell transfer in patients with ST-segment elevation myocardial infarction: double-blind, randomised controlled trial," Lancet, vol. 367, No. 9505, pp. 113-121 (Jan. 14, 2006).
Johnston, J. C., et al., "Minimum Requirements for Efficient Transduction of Dividing and Nondividing Cells by Feline Immunodeficiency Virus Vectors," Journal of Virology, vol. 73, No. 6, pp. 4991-5000 (Jun. 1999).
Lacoste, A., et al., "An Efficient and Reversible Transposable System for Gene Delivery and Lineage-Specific Differentiation in Human Embryonic Stem Cells," Cell Stem Cell, vol. 5, pp. 332-342 (Sep. 4, 2009).
Ludwig, T. E., et al., "Derivation of human embryonic stem cells in defined conditions," Nature Biotechnology, vol. 24, pp. 185-187 (2006).
Martin, M. J., et al., "Human embryonic stem cells express an immunogenic nonhuman sialic acid," Nat. Med., vol. 11, No. 2, pp. 228-232 (Feb. 2005).
Martinez-Salas, Encarncion, "Internal ribosome entry site biology and its use in expression vectors," Curr. Opin. Biotechnol., vol. 10, No. 5, pp. 458-464 (Oct. 1999).
Metallo, C. M., et al., "Directed Differentiation of Human Embryonic Stem Cells to Epidermal Progenitors," Methods Mol. Biol., vol. 585, pp. 83-92 (2010).
Morizane, A., et al., "From bench to bed: the potential of stem cells for the treatment of Parkinson's disease," Cell Tissue Res., vol. 331, No. 1, pp. 323-336 (2008).
Morling, F. J. and Russell, S. J., "Enhanced transduction efficiency of retroviral vectors coprecipitated with calcium phosphate," Gene Therapy, vol. 2, No. 7, pp. 504-508 (Sep. 1995).
Naldini, L., et al., "In vivo gene delivery and stable transduction of nondividing cells by a lentiviral vector," Science, vol. 272, No. 5259, pp. 263-267, 9 pages (Apr. 12, 1996).
Negre, D., et al., "Lentiviral Vectors Derived from Simian Immunodeficiency Virus," Current Topics in Microbiology and Immunology, vol. 261, pp. 53-74 (Feb. 2002).
Park, B., et al., "The Truncated Cytoplasmic Tail of HLA-G Serves a Quality-Control Function in Post-ER Compartments," Immunity, vol. 15, pp. 213-224 (Aug. 2001).
Pearson, T., et al., "Creation of "Humanized" Mice to Study Human Immunity," Curr. Protoc. Immunol., Chapter 15, Unit 15.21, 28 pages (May 2008).
Qureshi, Sohail A., "β-Lactamase: an ideal reporter system for monitoring gene expression in live eukaryotic cells," BioTechniques, vol. 42, pp. 91-96 (Jan. 2007).
Recillas-Targe, F., et al., "Position-effect protection and enhancer blocking by the chicken β-globin insulator are separable activities," PNAS, vol. 99, No. 10, pp. 6883-6888 (May 14, 2002).
Rouas-Freiss, N., et al., "The $\alpha_1$ domain of HLA-G1 and HLA-G2 inhibits cytotoxicity induced by natural killer cells: Is HLA-G the public ligand for natural killer cell inhibitory receptors?," Proc. Natl. Acad. Sci. USA, vol. 94, pp. 5249-5254 (May 1997).
Rousseau, P., et al., "The 14 bp Deletion-Insertion polymorphism in the 3' UT region of the HLA-G gene influences HLA-G mRNA stability," Human Immunology, vol. 64, No. 11, pp. 1005-1010 (Nov. 2003).
Running Deer, J. and Allison, D. S., "High-level expression of proteins in mammalian cells using transcription regulatory sequences from the Chinese hamster EF-1alpha gene," Biotechnol. Prog., vol. 20, No. 3, pp. 880-889 (May-Jun. 2004).
Sambrook, J. and Russell, D. W., "Molecular Cloning: A Laboratory Manual," Third Edition, Cold Spring Harbor Laboratory Press, Cold Spring Harbor, New York, 21 pages—Cover page, Copyright Page and Table of Contents Only (2001).
Sasaki H, Xu XC, Mohanakumar T. HLA-E and HLA-G expression on porcine endothelial cells inhibit xenoreactive human NK cells through CD94/NKG2-dependent and -independent pathways. J Immunol. Dec. 1, 1999;163(11):6301-5.
Shaner, N. C., et al., "Improved monomeric red, orange and yellow fluorescent proteins derived from *Discosoma* sp. red fluorescent protein," Nature Biotechnology, vol. 22, pp. 1567-1572 (2004).
Shcherbo, D., et al., "Bright far-red fluorescent protein for whole-body imaging," Nature Methods, vol. 4, pp. 741-746 (2007).
Supplementary European Search Report dated Feb. 24, 2016 for co-pending EP Application No. 13825511.2; 8 pages.
Swindle, C. S., et al., "Mutation of CpGs in the Murine Stem Cell Virus Retroviral Vector Long Terminal Repeat Represses Silencing in Embryonic Stem Cells," The Journal of Biological Chemistry, vol. 279, No. 1, pp. 34-41 (Jan. 2, 2004).

(56) References Cited

OTHER PUBLICATIONS

Szymczak, A. L., et al., "Correction of multi-gene deificiency in vivo using a single 'self-cleaving' 2A peptide-based retroviral vector," Nature Biotechnology, vol. 22, pp. 289-594 (2004).
Trompeter, H. I., et al., "Rapid and highly efficient gene transfer into natural killer cells by nucleofection," J. Immunol. Methods, vol. 274, No. 1-2, pp. 245-256 (Mar. 1, 2003).
Watanabe, K., et al., "A ROCK inhibitor permits survival of dissociated human embryonic stem cells," Nat. Biotechnol., vol. 25, No. 6, pp. 681-686, 7 pages (Jun. 2007).
Watson, J. D., et al., "Chapter 9: Controlling Eukaryotic Gene Expression", in Recombinant DNA, Second Edition, pp. 153-155, Scientific American Books, W.H. Freeman and Company, New York (2001) (6 pages).
Written Opinion and Search Report issued by the Intellectual Property Office of Singapore in SG11201500799Y, dated Sep. 21, 2016 (10 pages).
Zhao, L., et al., "Transforming Growth Factor β1 Induces Osteogenic Differentiation of Murine Bone Marrow Stromal Cells," Tissue Engineering Part A., vol. 16, No. 2, pp. 725-733 (Feb. 2010).
Teklemariam, Takele et al., "Heterologous Expression of Mutated HLA-G1 Reduces Alloreactivity of Human Dermal Fibroblasts," Regenerative Medicine, Future Medicine, UK, vol. 9, No. 6, Nov. 28, 2014, pp. 775-784 (10 pages).
Extended European Search Report dated Feb. 15, 2019 received in related European Patent Application No. 18211100.5 (15 pages).

| Antibody | wildtype | | eHLA-G-GFP | |
|---|---|---|---|---|
| | % reactivity (mean ± SEM) | MFI ratio (mean ± SEM) | % reactivity (mean ± SEM) | MFI ratio (mean ± SEM) |
| HLA-A,B,C | 98.3±0.5 | 123.5±9.1 | 98.3±0.4 | 132.1±9.2 |
| HLA-E | 2.4±0.4 | 0.8±0.1 | 4.0±0.6 | 0.8±0.1 |
| HLA-G | 8.0±1.0 | 1.0±0 | 58.6±6.2 | 7.1±1.4 |
| HLA-DP,DQ,DR | 29.7±3.2 | 3.7±0.9 | 29.3±1.9 | 3.6±0.2 |
| β2M | 99 | 364 | 99.0±0 | 357±51 |

Fig. 10

SEQUENCE LISTING

<160> NUMBER OF SEQ ID NOS: 7

<210> SEQ ID NO 1
<211> LENGTH: 338
<212> TYPE: PRT
<213> ORGANISM: Homo sapiens

<400> SEQUENCE: 1

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser

```
            100                 105                 110
Glu Ala Ser Ser His Thr Leu Gln Trp Met Ile Gly Cys Asp Leu Gly
            115                 120                 125

Ser Asp Gly Arg Leu Leu Arg Gly Tyr Glu Gln Tyr Ala Tyr Asp Gly
            130                 135             140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
                180                 185                 190

His Arg Tyr Leu Glu Asn Gly Lys Glu Met Leu Gln Arg Ala Asp Pro
            195                 200                 205

Pro Lys Thr His Val Thr His His Pro Val Phe Asp Tyr Glu Ala Thr
        210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
            275                 280                 285

Gly Leu Pro Glu Pro Leu Met Leu Arg Trp Lys Gln Ser Ser Leu Pro
        290                 295                 300

Thr Ile Pro Ile Met Gly Ile Val Ala Gly Leu Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 2
<211> LENGTH: 338
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
```

```
            115                 120                 125
Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Ala Ala Ser
                325                 330                 335

Ser Asp
```

<210> SEQ ID NO 3
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tgtgaaacag ctgccctgtg tgggactgag tggcaagtcc ctttgtgact tcaagaaccc    60
tgacttctct ttgtgcagag accagcccaa ccctgtgccc accatgaccc tcttcctcat   120
gctgaactgc attccttccc caatcacctt tcctgttcca gaaaaggggc tgggatgtct   180
ccgtctctgt ctcaaatttg tggtccactg agctataact tacttctgta ttaaaattag   240
aatctgagtg                                                         250

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
atttgttcat gcct                                                     14

<210> SEQ ID NO 5

<211> LENGTH: 264
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | |
|---|---|---|
| tgtgaaacag ctgccctgtg tgggactgag tggcaagatt tgttcatgcc ttccctttgt | 60 |
| gacttcaaga accctgactt ctctttgtgc agagaccagc ccaaccctgt gcccaccatg | 120 |
| accctcttcc tcatgctgaa ctgcattcct tccccaatca cctttcctgt tccagaaaag | 180 |
| gggctgggat gtctccgtct ctgtctcaaa tttgtggtcc actgagctat aacttacttc | 240 |
| tgtattaaaa ttagaatctg agtg | 264 |

<210> SEQ ID NO 6
<211> LENGTH: 1457
<212> TYPE: DNA
<213> ORGANISM: Cricetulus griseus

<400> SEQUENCE: 6

| | | |
|---|---|---|
| ggatggcggg gctgacgtcg ggaggtggcc tccacgggaa gggacacccg gatctcgaca | 60 |
| cagccttggc agtggagtca ggaagggtag gacagattct ggacgccctc ttggccagtc | 120 |
| ctcaccgccc cacccccgat ggagccgaga gtaattcata caaaaggagg gatcgccttc | 180 |
| gcccctggga atcccaggga ccgtcgctaa attctggccg gcctcccagc ccggaaccgc | 240 |
| tgtgcccgcc cagcgcggcg ggaggagcct gcgcctaggg cggatcgcgg gtcggcggga | 300 |
| gagcacaagc ccacagtccc cggcggtggg ggaggggcgc gctgagcggg ggcccgggag | 360 |
| ccagcgcggg gcaaactggg aaagtggtgt cgtgtgctgg ctccgccctc ttcccgaggg | 420 |
| tgggggagaa cggtataaaa gtgcggtagt cgcgttggac gttcttttc gcaacgggtt | 480 |
| tgccgtcaga acgcaggtga gtggcggtg tggcctccgc gggcccgggc tccctccttt | 540 |
| gagcggggtc ggaccgccgt gcgggtgtcg tcggccgggc ttctctgcga gcgttcccgc | 600 |
| cctggatggc gggctgtgcg ggagggcgag gggggaggc ctggcggcgg ccccggagcc | 660 |
| tcgcctcgtg tcgggcgtga ggcctagcgt ggcttccgcc ccgccgcgtg ccaccgcggc | 720 |
| cgcgctttgc tgtctgcccg gctgccctcg attgcctgcc cgcggcccgg gccaacaaag | 780 |
| ggagggcgtg gagctggctg gtagggagcc ccgtagtccg catgtcggc agggagagcg | 840 |
| gcagcagtcg gggggggac cgggcccgcc cgtcccgcag cacatgtccg acgccgcctg | 900 |
| gacgggtagc ggcctgtgtc ctgataaggc ggccgggcgg tgggttttag atgcgggtt | 960 |
| caggtggccc cgggtcccgg cccggtctgg ccagtacccc gtagtggctt agctccgagg | 1020 |
| agggcgagcc cgcccgcccg gcaccagttg cgtgcgcgga agatggccg ctcccggcc | 1080 |
| ctgtagcaag gagctcaaaa tggaggacgc ggcagcccgg cggagcgggg cggtgagtc | 1140 |
| acccacacaa aggaagaggg ccttgcccct cgccggccgc tgcttcctgt gacccgtgg | 1200 |
| tgtaccggcc gcacttcagt caccccgggc gctctttcgg agcaccgctg gcctccgctg | 1260 |
| ggggagggga tctgtctaat ggcgttggag tttgctcaca tttggtgggt ggagactgta | 1320 |
| gccaggccag cctggccatg gaagtaattc ttggaatttg cccattttga gtttggagcg | 1380 |
| aagctgattg acaaagctgc ttagccgttc aaaggtattc ttcgaacttt ttttttaagg | 1440 |
| tgttgtgaaa accaccg | 1457 |

<210> SEQ ID NO 7

```
<211> LENGTH: 243
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gagctcacgg ggacagcccc cccccaaagc ccccagggat gtaattacgt ccctcccccg      60
ctagggggca gcagcgagcc gcccggggct ccgctccggt ccggcgctcc ccccgcatcc     120
ccgagccggc agcgtgcggg gacagcccgg gcacggggaa ggtggcacgg gatcgctttc     180
ctctgaacgc ttctcgctgc tctttgagcc tgcagacacc tgggggatac ggggaaaaag     240
ctt                                                                   243
```

HLA G-MODIFIED CELLS AND METHODS

CROSS-REFERENCE TO RELATED APPLICATIONS

This application is a continuation of U.S. patent application Ser. No. 14/608,004 filed Jan. 28, 2015 and issued as U.S. Pat. No. 9,714,280, which is a continuation of International Patent Application No. PCT/US2013/052767 filed Jul. 30, 2013, which claims the benefit of and priority to U.S. Provisional Patent Application Ser. No. 61/677,739, filed Jul. 31, 2012, the disclosure of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 16, 2017, is named 2017-06-16_126_US3_Sequence_Listing.txt and is 10,153 bytes in size.

BACKGROUND OF THE INVENTION

Regenerative medicine in the form of cell transplantation is one of the most promising therapeutic approaches for the treatment of intractable medical conditions such as diabetes, heart disease, and neurodegenerative diseases. However, a major hurdle towards implementing cell transplantation in the clinic is immune rejection of donor cells, especially when these are derived from a foreign host. While it is possible to address immune rejection, in part, by administering immunosuppressant drugs, these entail severe adverse side effects. Thus, there is an ongoing need to develop improved technologies for cell transplantation therapies.

SUMMARY OF THE INVENTION

Disclosed herein are cell-based compositions and methods for cell transplantation therapy based on the long-term forced expression of at least an exogenous HLA-G protein in donor cells to be transplanted into a subject in need of such donor cells. The invention provides data that shows that cells (whether pluripotent or differentiated) modified to express exogenous HLA-G in the manner described herein have reduced immunogenicity and/or increased immunosuppression. The reduced immunogenicity and/or increased suppression abilities provided by the HLA-G genetic modification are stable and persist over long periods of time, including through processes of differentiation. The implication is that the HLA-G modified cells of the invention can serve as universal donor cells or tissue (i.e., reducing or eliminating the requirement for matching the type of classical human leukocyte antigen (HLA) class I and class II molecules between donor cells and the recipient) for numerous injuries, diseases, or disorders.

Accordingly, in one aspect described herein is a genetically modified mammalian cell (an HLA-G modified cell) that has reduced immunogenicity and/or is capable of providing increased immunosuppression in an allogeneic recipient as compared to the mammalian cell without said genetic modification, where (i) the genetically modified mammalian cell comprises: (a) an exogenous nucleic acid (e.g., an expression vector) comprising a nucleic acid sequence encoding an HLA-G protein having an amino acid sequence at least 85% identical to human HLA-G, and comprising one or more amino acid mutations that reduce retention of HLA-G in the endoplasmic reticulum-golgi recycling pathway, and/or (b) a 3' UTR (untranslated region) sequence that does not contain microRNA binding sites such as SEQ ID NO:3 or a sequence that does not comprise SEQ ID NO:4; and (ii) the encoded HLA-G protein is expressed by the genetically modified mammalian cell for at least seven weeks (e.g., at least 20 weeks or at least 50 weeks).

In other embodiments, the invention provides a genetically modified mammalian cell that has reduced immunogenicity and/or improved immunosuppression as compared to the mammalian cell without said genetic modification, wherein: (i) the genetically modified mammalian cell comprises an exogenous nucleic acid comprising: (a) a nucleic acid sequence (such as SEQ ID NO:2) encoding an HLA-G protein having an amino acid sequence at least 95% identical to consensus wild-type human HLA-G (such as SEQ ID NO:1), and comprising one or more amino acid mutations that reduce retention of HLA-G in the endoplasmic reticulum-golgi recycling pathway; and (b) a 3' untranslated region (UTR) (such as SEQ ID NO:3) that is at least 85% identical to the 3' untranslated region sequence of the consensus wild-type human HLA-G gene and does not comprise SEQ ID NO:4; and (ii) the encoded HLA-G protein is expressed by the genetically modified mammalian cell for at least seven weeks.

In some embodiments, a genetically modified cell has reduced immunogenicity and/or improved immunosuppression if it shows: (1) a reduction of NK-92 cytotoxicity of the genetically modified cell as compared to the mammalian cell without said genetic modification, (2) a reduction of in vitro peripheral blood mononuclear cell proliferation of the genetically modified cell as compared to the mammalian cell without said genetic modification, and/or (3) an increase in the size and weight of tumor formation by the genetically modified cell as compared to the mammalian cell without said genetic modification in humanized NSG mice.

In some embodiments, the genetically modified mammalian cell does not have matches (i.e., same allele(s)) in one or more HLA antigens as compared to the allogeneic recipient, wherein the HLA antigens are selected from the group consisting of HLA-A, HLA-B, HLA-C, HLA-DP, HLA-DQ, and HLA-DR. In certain embodiments, the genetically modified mammalian cell only has 1, 2, 3, 4, or 5 matches in one or more HLA antigens as compared to the allogeneic recipient, wherein the HLA antigens are selected from the group consisting of HLA-A, HLA-B, HLA-C, HLA-DP, HLA-DQ, and HLA-DR. In one embodiment, the genetically modified mammalian cell has no matches in with the allogeneic recipient with respect to HLA-A, HLA-B, HLA-C, HLA-DP, HLA-DQ, and HLA-DR.

In some embodiments, the genetically modified cell comprises an HLA-G transgene without one or more amino acid mutations that reduce retention of HLA-G in the endoplasmic reticulum-golgi recycling pathway (i.e., an HLA-G wild-type consensus sequence such as SEQ ID NO:1), but has an HLA-G transgene that comprises a 3' UTR (untranslated region) sequence that does not contain microRNA binding sites such as SEQ ID NO:3, or a sequence that does not comprise SEQ ID NO:4.

In some embodiments, the one or more mutations that reduce retention of HLA-G in the endoplasmic reticulum-golgi recycling pathway include a di-Lysine (KK) motif mutation. In some embodiments, the KK motif mutation incudes a K334A mutation, a K335A mutation, or both mutations.

In some embodiments, the exogenous nucleic acid to be expressed in the genetically modified cell includes a 3' UTR sequence that does not contain SEQ ID NO.4. In one embodiment, where the 3' UTR sequence of the exogenous nucleic acid does not include SEQ ID NO:4, the nucleic acid sequence contains SEQ ID NO:3.

In some embodiments, the expressed HLA-G is present on the cell surface of the genetically modified mammalian cell.

In some embodiments, the genetically modified mammalian cell is a human cell, a mouse cell, a rat cell, a monkey cell, or a pig cell.

In some embodiments, the genetically modified mammalian cell is a stem cell, a progenitor cell, or a cell obtained by directed differentiation of the stem cell or the progenitor cell. In some embodiments, the genetically modified mammalian cell is a cell that was already differentiated (whether naturally or in vitro) prior to introduction of an exogenous HLA-G transgene. In some embodiments, the genetically modified mammalian cell is a stem cell (e.g., a pluripotent stem cell). In some embodiments, where the genetically modified mammalian cell is a stem cell, the stem cell is an embryonic stem cell, an induced pluripotent stem cell, or a totipotent stem cell. In some embodiments, the genetically modified mammalian cell is an embryonic stem cell. In another embodiment, the genetically modified mammalian cell is an induced pluripotent stem cell. In a further embodiment, the genetically modified mammalian cell is not of an immune system cell type. In another embodiment, the genetically modified mammalian cell is a cell obtained by in vitro differentiation of a stem cell or a progenitor cell wherein the stem cell or progenitor cell is genetically modified and then differentiated in vitro.

In other embodiments, the genetically modified cell is a fully differentiated cell, an epidermal progenitor cell, a pancreatic progenitor cell, a hematopoietic stem cell, a cell obtained by differentiation of the pluripotent stem cell, a keratinocyte, a fibroblast, a mesenchymal stem cell, a cardiomyocyte, a neural stem cell, a neuron, an astrocyte, or a pancreatic β cell progenitor.

In some embodiments, where the exogenous nucleic acid in the genetically modified mammalian cell is an expression vector, the expression vector is a transposon vector or a retroviral vector. In some embodiments, where the exogenous nucleic acid is an expression vector, the expression vector is a targeting vector, and the genetically modified mammalian cell was obtained by homologous recombination of the targeting vector. In some embodiments, the expression vector may further include a nucleic acid sequence encoding a reporter protein such as green fluorescent protein (GFP).

In some embodiments, the exogenous nucleic acid also includes a nucleic acid sequence that (i) is at least 85% identical to the 3' untranslated region sequence of the human, HLA-G gene; and (ii) comprises at least one mutation that inhibits binding of a cognate microRNA to the mutated site within an mRNA comprising the mutated binding site within its 3' untranslated region. In one embodiment, such a nucleic acid sequence comprises SEQ ID NO:3.

In some embodiments an artificial tissue is provided that contains the genetically modified cell.

In another aspect provided herein is an isolated nucleic acid that includes (i) a first nucleic acid sequence that encodes an amino acid sequence at least 85% identical to human, HLA-G; and (ii) a second nucleic acid sequence that is at least 85% identical to the 3' untranslated region sequence of the human HLA-G gene and operably linked to the first nucleic acid sequence, where the amino acid sequence comprises a mutation that reduces retention of HLA-G in the endoplasmic reticulum-golgi recycling pathway, and the second nucleic acid sequence comprises at least one mutation that inhibits binding of a cognate microRNA to an mRNA comprising the mutated binding site within its 3' untranslated region.

In some embodiments, the 3' untranslated region sequence of the isolated nucleic acid does not comprise SEQ ID NO:4. In one embodiment, where the 3' untranslated region sequence does not comprise SEQ ID NO:4, the 3' untranslated region sequence comprises SEQ ID NO:3.

In some embodiments, a mammalian expression vector is provided that includes the isolated nucleic acid and a promoter operably linked to the first nucleic acid sequence, wherein the promoter is not silenced in a stem cell. In some embodiments, the promoter contains the nucleic acid sequence of the Chinese hamster EF-1α (CHEF-1α) promoter or human EF-1α promoter. In one embodiment, the CHEF-1α promoter comprises SEQ ID NO:6. In other embodiments, the promoter used to drive expression of an HLA-G transgene is a tissue or cell type-selective promoter. In some embodiments, the mammalian expression vector includes comprising a third nucleic acid sequence encoding a reporter protein. In some embodiments, the mammalian expression vector is a transposon vector. In some embodiments, a genetically modified mammalian cell is provided that contains the mammalian expression vector.

In some embodiments, an isolated nucleic acid is provided that comprises: (i) a first nucleic acid sequence that encodes an amino acid sequence at least 95% identical to human HLA-G, wherein the amino acid sequence comprises a mutation that reduces retention of HLA-G in the endoplasmic reticulum-golgi recycling pathway; and (ii) a second nucleic acid sequence that is at least 95% identical to the 3' untranslated region sequence of the human HLA-G gene and operably linked to the first nucleic acid sequence, wherein the second nucleic acid sequence comprises at least one mutation that inhibits binding of a cognate microRNA to an mRNA comprising the mutated binding site within its 3' untranslated region. In one embodiment, the first nucleic acid sequence encodes an amino acid sequence of SEQ ID NO:2. In another embodiment, the second nucleic acid sequence does not comprise SEQ ID NO:4. In one embodiment, the second nucleic acid sequence comprises SEQ ID NO:3. In another embodiment, a mammalian expression vector is provided that comprises said first and second nucleic acid sequences, and further comprises a promoter operably linked to the first nucleic acid sequence, wherein the promoter is not silenced in a stem cell or a in a cell generated by differentiation of the stem cell. Such a promoter can comprise the nucleic acid sequence of the Chinese hamster EF-1α promoter. In another embodiment, the mammalian expression vector further comprises a nucleic acid sequence encoding a reporter protein. In another embodiment, the mammalian expression vector is a transposon vector. In another embodiment, the mammalian expression vector comprises all of the elements shown in FIG. 1.

In one embodiment, a mammalian expression vector is provided that comprises: (a) a Chinese hamster EF-1α promoter, (b) a nucleic acid sequence that is operably linked to the promoter and that encodes human HLA-G with an amino acid sequence of SEQ ID NO:2, and (c) a 3'UTR sequence comprising SEQ ID NO:3. In some embodiments, a genetically modified mammalian cell is provided that comprises such an expression vector.

In various embodiments, HLA-G modified mammalian cells (e.g., human HLA-G modified cells) are administered to a subject suffering from any of a number of conditions including, but not limited to cardiovascular disease, eye disease (e.g., macular degeneration), auditory disease, (e.g., deafness), diabetes, neurodegenerative disease, Alzheimer's Disease, Parkinson's Disease, multiple sclerosis, osteoporosis, liver disease, kidney disease, autoimmune disease, arthritis, gum disease, a dental condition, or a proliferative disorder (e.g., a cancer). In other cases, the subject is suffering from, or at high risk of suffering from, an acute health condition, e.g., stroke, spinal cord injury, burn, or a wound. In other cases, the subject is suffering from loss of tissue such as lipatrophy or aging-related losses in collagen. In other cases, the subject suffers from a non-healing ulcer, or is need for an agent to assist in closure of defects like hypospadias and epispadias. In other cases, the subject is in need for a permanent or temporary skin graft for wound healing or for skin substitutes.

In some embodiments, the invention provides a universal method of cellular or tissue repair or regeneration to a subject in need thereof, the method comprising injecting or grafting to the subject a cellular or tissue composition comprising a population of enhanced HLA-G ("eHLA-G") modified cells, wherein the subject has at least one mismatched classical HLA class I or HLA class II molecule as compared to the population of eHLA-G modified cells, and wherein the population of eHLA-G modified cells exhibits reduced immunogenicity and/or improved immunosuppression as compared to cells of the same-type without the eHLA-G modification. The reduced immunogenicity and/or improved immunosuppression can be determined, for example, by comparing the eHLA-G modified cell to a control cell of the same type without the eHLA-G modification in an NK-92 cytotoxicity assay, a humanized NSG tumor growth assay, and/or a PBMC proliferation assay. In one embodiment, the population of genetically modified cells comprises a population of eHLA-G genetically modified human dermal fibroblasts. In another embodiment, the population of genetically modified cells comprises a population of eHLA-G genetically modified human epidermal progenitors. In another embodiment, the population of genetically modified cells comprises a population of eHLA-G genetically modified human mesenchymal stem cells. In another embodiment, the population of genetically modified cells comprises a population of eHLA-G genetically modified human embryonic stem (ES) cells. In another embodiment, the population of genetically modified cells comprises a population of cell differentiated in vitro from eHLA-G genetically modified human embryonic stem cells. In other embodiments, the population of genetically modified cells are not rejected by the subject's immune system for at least 2, 4, 6, 8, 10, 12, 14, 16, 18, 20, 24, 36, 48, or 52 weeks.

In another embodiment, the invention provides a method for regenerating skin to a subject in need thereof, the method comprising injecting a population of eHLA-G modified dermal fibroblasts and/or eHLA-G modified embryonic epidermal progenitors to a site of skin injury on the subject, wherein the subject has at least one mismatched classical HLA class I or HLA class II molecule as compared to the population of eHLA-G modified dermal fibroblasts and/or eHLA-G modified embryonic epidermal progenitors.

In another embodiment, a cell therapy method is provided that comprises administering to a subject in need thereof a population of genetically modified mammalian cells comprising an exogenous human β2-microglobulin (β2m) molecule and an eHLA-G transgene of the invention.

BRIEF DESCRIPTION OF THE DRAWINGS

FIG. 9B (Bottom Panel) shows surface HLA-G expression eHLA-G(MSCV)-GFP modified hESCs. These data indicate HLA-G is highly expressed when the transgene is operably linked to the EF-1α promoter, in contrast the minimal expression when the transgene is under control of the MSCV promoter. See also FIG. 15 for additional data showing that HLA-G transgene expression is significantly influenced by promoter activity.

FIG. 10 shows that expression of HLA class I and class II is similar on wildtype and eHLA-G+ hESCs. The table compares expression levels of various HLA variants and β2 microglobulin in wildtype versus HLA-G modified hESCs.

(Note: as used herein, an "mHLA-G(EF-1α)-GFP" transgene is synonymous with "eHLA-G(EF-1α)-GFP".) This data shows that HLA-G transgene expression imparts immunosuppressive and/or reduced immunogenicity characteristics in hESCs. See Example 6 for further description.

Figure 19:
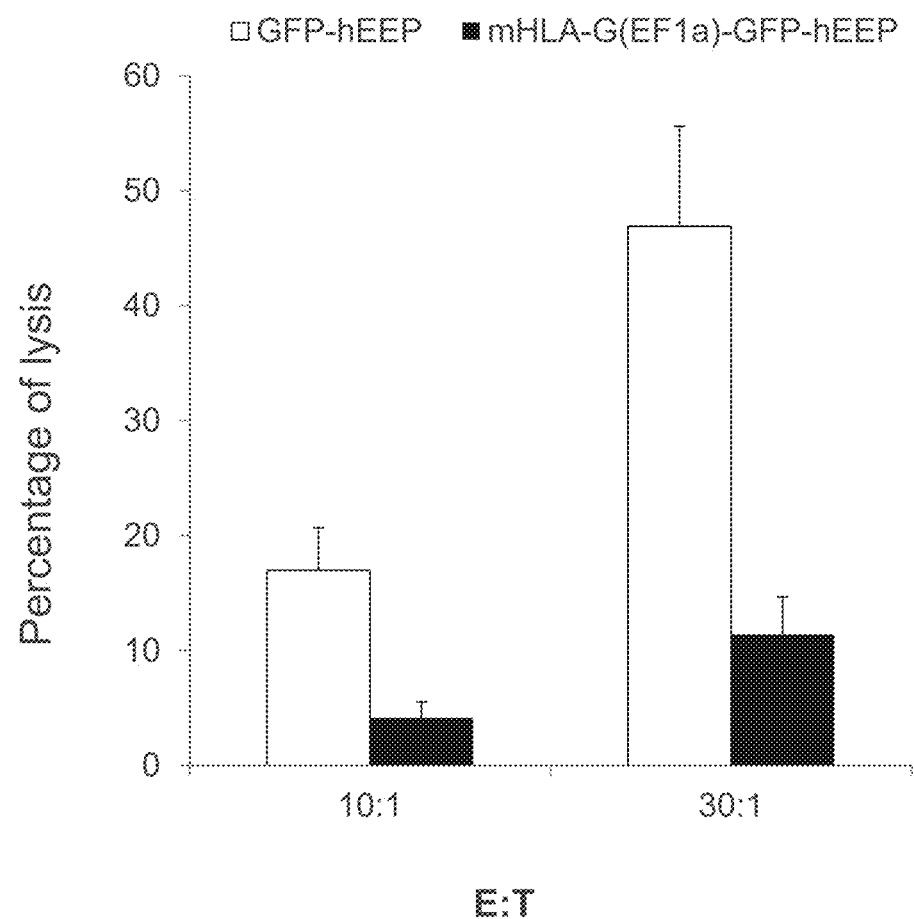

FIG. 19. NK cytotoxicity experiments were conducted on hEEPs differentiated from hESCs. As shown, killing of eHLA(EF-1α)-GFP-hEEPs was reduced well more than 100% (about 3-fold) as compared to control hEEPs. This data shows that HLA-G transgene expression imparts immunosuppressive and/or reduced immunogenicity characteristics in differentiated cells, which also shows that these enhanced functional immune evasion characteristics of HLA-G expression via the eHLA-G transgene survived the directed differentiation process. See Example 6 for further description.

Figure 20:
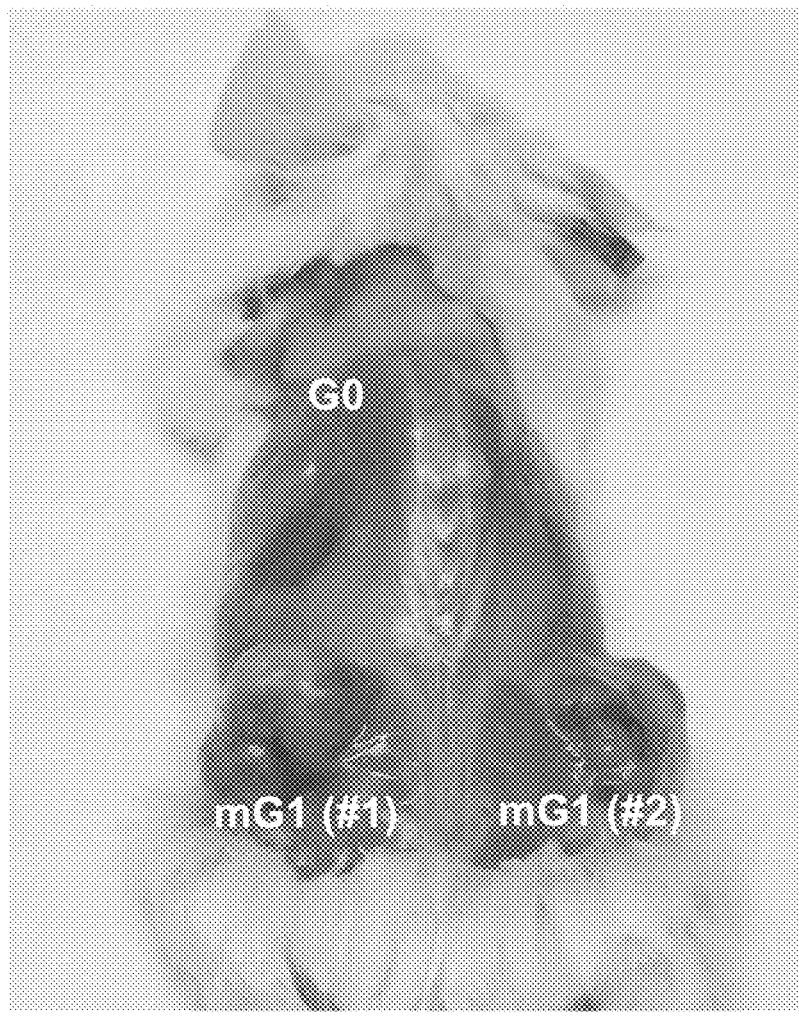

FIG. 20 shows the results of hESC allografts in humanized mice. The "G0" hESCs were the control wild-type hESCs that do not contain an eHLA-G transgene, but rather only GFP. "mG1(#1)" and "mG1(#2)" refer to two different eHLA-G(EF-1α)-GFP nucleofected hESC clones. The G0, mG1(#1), and mG1(#2) tumors as shown were measured and weighed. The G0 hESCs formed a tumor with a volume of 126.9 cubic millimeters and a weight of 32 milligrams. The mG1(#1) hESCs formed a tumor with a volume of 748.4 cubic millimeters and a weight of 318 milligrams. The mG1(#2) hESCs formed a tumor with a volume of 1116.7 cubic millimeters and a weight of 675 milligrams. See Example 7 for further description.

Figure 21:
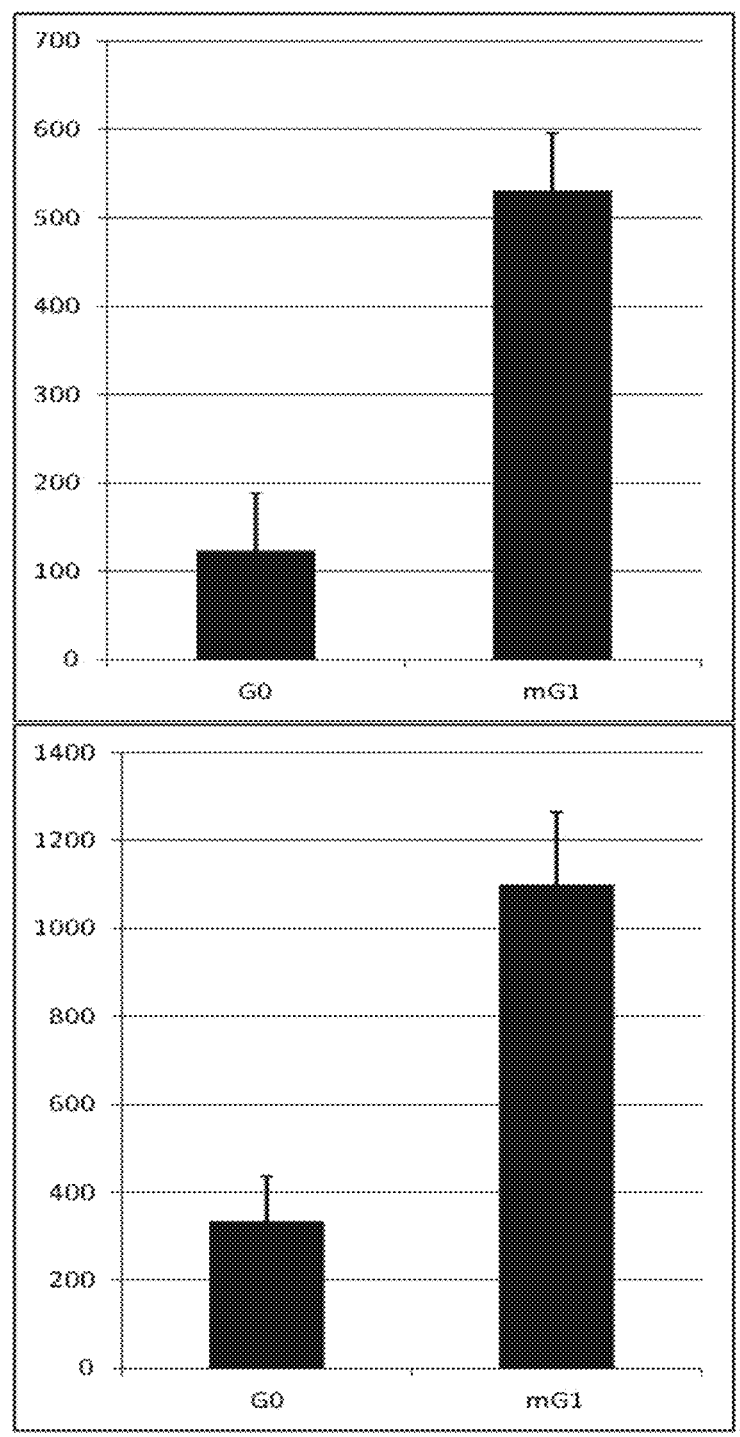

FIG. 21 shows the averaged results of tumors from hESC allografts onto five humanized NSG mice. Top panel shows tumor weight (mg) results. The bottom panel shows tumor volume (cubic millimeters) results. The data shows that HLA-G nucleofected hESCs ("mG1") formed much larger (more than 3-fold by volume) and heavier (more than 2-fold by weight) tumors than wild-type hESCs ("G0") transplanted into humanized NSG mice. This indicates that HLA-G transgene expression can provide reduced immunogenicity and/or increased immunosuppression in an allograft human environment (i.e., NSG humanized mice). This data, along with the NK92 cytotoxicity studies, supports the general application of the eHLA-G transgene constructs described herein for modifying any desired cell-type into a universal or superior allogeneic donor for therapy, transplants, tissue repair, cell and tissue substitutes, and the like. See Example 7 for further description.

FIG. 22. Human dermal fibroblasts stably transfected with the eHLA-G(EF-1α)-GFP transgene ("HFD-m1-GFP" cells) or GFP-alone control construct ("HFD-G0-GFP" cells) were assessed for their ability to inhibit PBMC proliferation. As shown, the HFD-mG1-GFP clone "mG1-R1" suppressed PBMC proliferation greater than controls and other clones, indicating that exogenous HLA-G expression can provide immunosuppression for differentiated cells, such as fibroblasts. See Example 9 for further description, including a summary of NK-92 cytotoxicity studies with HFD-m1-GFP and controls, which shows that the eHLA-G modification to human dermal fibroblasts reduced their immunogenicity. Thus, these data further support the use of the eHLA-G transgene constructs described herein for modifying any desired cell-type, whether pluripotent, multipotent, or fully differentiated, into a universal or superior allogeneic donor for therapy, transplants, tissue repair, cell and tissue substitutes, and the like.

DETAILED DESCRIPTION

The present disclosure features genetically modified mammalian cells that express exogenous HLA-G persistently (HLA-G modified cells), as well as nucleic acid compositions to generate such modified mammalian cells. The eHLA-G genetic modifications described herein provide the cells with characteristics of reduced immunogenicity and/or improved immunosuppression, such that these cells have the promise of being universal or improved donor cells for transplants, cellular and tissue regeneration or reconstruction, and other therapies.

I. Compositions:

A. Genetically Modified Mammalian Cells that Express Exogenous HLA-G

As described herein, a wide range of mammalian cell types that express exogenous HLA-G (HLA-G modified cells) can be generated. Such cell types include, but are not limited to, totipotent cells, embryonic stem cells (e.g., human embryonic stem cells), induced pluripotent stem cells (e.g., human induced pluripotent stem cells), multipotent stem cells, epidermal progenitor cells, mesenchymal stem cells, pancreatic β cell progenitors, pancreatic β cells, cardiac progenitors, cardiomyocytes, hepatic progenitors, hepatocytes, muscle cell progenitors, muscle cells, kidney cells, osteoblasts, hematopoietic progenitors, dental follicle cells, hair follicle cells, retinal pigment epithelial cells, neural stem cells, neurons, astrocytes, oligodendrocytes, inner ear cells, and fibroblasts (including human dermal fibroblast (HFD)). In some embodiments, the HLA-G modified cells are not cells having an immune system cell type. Such mammalian cells can be derived from one of several species including, e.g., human, mouse, rat, monkey, or pig. In essence, any cell-type can be transfected with the constructs described herein and then tested for HLA-G expression and how such expression can impart reduced immunogenicity and/or improved immunosuppression to the modified cell.

In some embodiments, to obtain a substantially enriched population of HLA-G modified cells of a desired cell type, a genetically modified pluripotent stem cell line such as a human embryonic stem cell line, or a human induced pluripotent stem cell line, or any cell line that has multipotent traits including mesenchymal stem cells and immune system progenitor cells, that expresses HLA-G is generated and then subjected to directed differentiation to obtain a cell population that expresses HLA-G and that is substantially enriched for a desired cell type. In some embodiments, the substantially enriched cell population includes at least about 2% to about 100% of the desired cell type, e.g., at least about 3%, 4%, 5%, 7%, 8%, 10%, 20%, 22%, 25%, 35%, 40%, 45%, 50%, 60%, 70%, 75%, 80%, 85%, or another percentage of the desired cell type from at least about 2% to about 100%. Methods for enriching cells of a desired cell type are known in the art. See, e.g., U.S. patent application Ser. No. 12/532,512.

Methods for obtaining human embryonic stem cells or induced pluripotent stem cells are known in the art, as described in, e.g., U.S. Pat. Nos. 6,200,806 and 7,217,569 (for human embryonic stem cell derivation) and U.S. Pat. Nos. 8,048,999, 8,058,065, and 8,048,675 (for generation of human induced pluripotent stem cells).

Genetically modified mammalian pluripotent or multipotent stem cell lines, e.g., human embryonic stem cells or human induced pluripotent stem cells, etc., and also fully differentiated genetically modified mammalian, that stably express an HLA-G protein encoded by one of the nucleic acids described herein are generated by any of a number of methods known in the art. In some embodiments, the cell line is genetically modified by stable transfection with one or more nucleic acid expression vectors (e.g., a plasmid vector or a minicircle vector) that include an expression cassette for expression of an HLA-G protein as described herein, a selection marker, and optionally a reporter protein. Examples of suitable selection markers encoded by such vectors include proteins that confer resistance to a selection agent. Such proteins and their corresponding selection agents include, without limitation, puromycin N-acetyltransferase (puromycin), hygromycin phosphotransferase (hygromycin), blasticidin-S-deaminase (blasticidin), and neomycin phosphotransferase (neomycin). Selection with the appropriate selection agent may last for at least about 3 to about 14 days, e.g., about 4, 5, 6, 7, 8, 9, 10, 12, 13, or another period from about 3 to about 14 days until resistant colonies are apparent.

Examples of suitable fluorescent reporter proteins include, but are not limited to, EGFP and its variants such as YFP, Cyan, and dEGFPs; DS-Red, monomeric Orange, the far-red fluorescent protein "Katushka" (Shcherbo et al (2007), *Nat Methods,* 4:741-746), or variants of any of the foregoing. In other embodiments, the reporter is an enzyme that converts a substrate that, in the process, yields a detectable signal, e.g., a fluorescent or luminescent signal in the presence of a fluorogenic or luminogenic substrate, respectively. For example, in some embodiments, the selection marker enzyme comprises the amino acid sequence of a luciferase, e.g., a firefly luciferase, click beetle luciferase, or Renilla luciferase. Luciferase activity can be detected by providing an appropriate luminogenic substrate, e.g., firefly luciferin for firefly luciferase or coelenterazine for Renilla luciferase. Luciferase activity in the presence of an appropriate substrate can be quantified by luminometry to assay total luciferase activity of whole cell populations in culture dish wells, or, alternatively, luciferase activity of individual cells or colonies can be detected by use of a microscope in combination with a photon counting camera. Details of luciferase assays, including high-throughput methods, are disclosed in, e.g., U.S. Pat. Nos. 5,650,135, 5,744,320, and 6,982,431. In other embodiments, the reporter enzyme comprises the amino acid sequence of a modified beta-lactamase, the expression of which can be detected and quantified in living cells by a ratiometric fluorescence assay for breakdown of fluorogenic beta-lactam substrates as described in, e.g., U.S. Pat. Nos. 5,741,657, 6,031,094, and U.S. Patent Publication No. 20070184513. See also Qureshi (2007), *Biotechniques,* 42(1):91-96 for a review. Other suitable reporter enzymes include, but are not limited to, the HaloTag® hydrolase (Promega, Madison, Wis., as described in, e.g., U.S. Pat. No. 7,238,842 and Patent Publication Nos. 20080026407 and 20080145882) and beta.-galactosidase.

In some embodiments, the genetically modified mammalian cells are also genetically modified to express a human β2 microglobulin (GenBank Accession No. AY187687.1). Without wishing to be bound by theory, it is believed that expression of human β2 microglobulin will enhance surface expression of transgenic HLA-G in the genetically modified mammalian cells.

In some embodiments, the nucleic acid expression vector is a transposon vector that includes transposition elements that facilitate integration of the transposition of the transposon vector into a host genome when introduced into a host cell in the presence of a cognate transposase (e.g., the piggyBAC transposase), as described in, e.g., U.S. patent application Ser. No. 12/728,943. Transposon expression vectors (e.g., PiggyBac vectors) as well as transposase expression vectors are commercially available from, e.g., System Biosciences (Mountain View, Calif.). In some embodiments, where a transposon vector is used, no selection marker or reporter protein expression cassette are necessary to generate a stably transfected, HLA-G modified cell line, as the efficiency of transfection by such vectors is sufficiently high to obviate the need for a selection marker. Alternatively, the expression vector may be a targeting vector, which allows site-specific integration of the eHLA-G transgene in the host cell genome. The design and use of targeting vectors is routine in the art as exemplified by U.S. Pat. No. 5,464,764.

Methods for preparation of transfection-grade nucleic acid expression vectors and transfection methods are well established. See, e.g., Sambrook and Russell (2001), "Molecular Cloning: A Laboratory Manual," 3rd ed., (CSHL Press); and Current Protocols in Molecular Biology, John Wiley & Sons, N.Y. (2005), 9.1-9.14. Examples of high efficiency transfection efficiency methods include "nucleofection," as described in, e.g., Trompeter (2003), *J Immunol. Methods,* 274(1-2):245-256, and in U.S. Pat. Nos. 7,332,332, 8,003,389; 8,039,259, and 8,192,990 9, transfection with lipid-based transfection reagents such as Fugene® (Roche), DOTAP, and Lipofectamine™ (Invitrogen).

In other embodiments, genetically modified cells, e.g., differentiated, multipotent, pluripotent, or totipotent stem cell lines, are generated by transduction with a recombinant virus. Examples of suitable recombinant viruses include, but are not limited to, retroviruses (including lentiviruses); adenoviruses; and adeno-associated viruses. Often, the recombinant retrovirus is murine moloney leukemia virus (MMLV), but other recombinant retroviruses may also be used, e.g., Avian Leukosis Virus, Bovine Leukemia Virus, Murine Leukemia Virus (MLV), Mink-Cell focus-Inducing Virus, Murine Sarcoma Virus, Reticuloendotheliosis virus, Gibbon Ape Leukemia Virus, Mason Pfizer Monkey Virus, or Rous Sarcoma Virus, see, e.g., U.S. Pat. No. 6,333,195.

In other cases, the recombinant retrovirus is a lentivirus (e.g., Human Immunodeficiency Virus-1 (HIV-1); Simian Immunodeficiency Virus (SIV); or Feline Immunodeficiency Virus (FIV)), See, e.g., Johnston et al., (1999), Journal of Virology, 73(6):4991-5000 (FIV); Negre et al., (2002), *Current Topics in Microbiology and Immunology,* 261:53-74 (SIV); Naldini et al., (1996), *Science,* 272:263-267 (HIV).

The recombinant retrovirus may comprise a viral polypeptide (e.g., retroviral env) to aid entry into the target cell. Such viral polypeptides are well-established in the art, see, e.g., U.S. Pat. No. 5,449,614. The viral polypeptide may be an amphotropic viral polypeptide, e.g., amphotropic env, that aids entry into cells derived from multiple species, including cells outside of the original host species. See, e.g., id. The viral polypeptide may be a xenotropic viral polypeptide that aids entry into cells outside of the original host species. See, e.g., id. In some embodiments, the viral polypeptide is an ecotropic viral polypeptide, e.g., ecotropic env, that aids entry into cells of the original host species. See, e.g., id.

Viral transduction of cells may be accomplished by any method known in the art. e.g., Palsson, B., et al., (1995), WO95/10619; Morling, F. J. et al., (1995), *Gene Therapy,* 2:504-508; Gopp et al., (2006), *Methods Enzymol,* 420:64-81. For example, the infection may be accomplished by spin-infection or "spinoculation" methods that involve subjecting the cells to centrifugation during the period closely following the addition of virus to the cells. In some cases, virus may be concentrated prior to the infection, e.g., by ultracentrifugation.

The multiplicity of infection (m.o.i.) used to transduce the cells to be genetically modified can range from about 1 m.o.i. to about 50 m.o.i., e.g., about 1 m.o.i., about 5 m.o.i., about 7.5; m.o.i., about 10 m.o.i., about 15 m.o.i., about 20 m.o.i., about 30 m.o.i., about 40 m.o.i., or about 50 m.o.i.

Methods for generating various cell types from pluripotent stem cells (e.g., human embryonic stem cells or human induced pluripotent stem cells) by directed differentiation are known in the art, as described in, e.g., U.S. Pat. Nos. 7,955,849, 7,763,466, 7,264,968; and U.S. patent application Ser. Nos. 12/179,462, and 12/187,543.

In one exemplary embodiment, human embryonic epidermal progenitors (hEEPs) are derived from a human pluripotent stem cell line, e.g., human embryonic stem cells or human induced pluripotent stem cells as follows.

Pluripotent stem cells are maintained in Embryonic Stem Cell (ESC) growth medium containing DMEM/F12 (1:1) supplemented with 20% knockout serum replacement, 0.1 mM MEM non-essential amino acids, 1 mM GlutaMax, 0.1 mM β-mercaptoethanol (Sigma). ESC growth medium is conditioned by plating mitotically inactivated mouse embryonic fibroblasts (MEFs) (CF-1, ATCC) at a density of $5\times10^4$ cells/cm$^2$ and incubating for 18-24 hours. After conditioning, 4 ng/ml bFGF is added and the completely conditioned medium is sterile filtered. hESCs are subcultured every 5-6 days (at a 1:3 or 1:4 split) on Matrigel® (BD Biosciences)-coated plates using 1 mg/ml Dispase to remove cell colonies. hEEPs Differentiation of pluripotent stem cells into K14$^+$/p63$^+$ hEEPs, by first culturing the pluripotent stem cells in 6-well plates for 4 days in ESC growth medium and then changing over to 2 ml/well of differentiation medium, comprised of unconditioned hESC growth medium containing 1 µM all-trans retinoic acid (Sigma) and 25 ng/ml BMP4. After daily medium changes for 7 days, cells are treated with dispase, centrifuged, and resuspended in defined keratinocyte serum-free medium (DSFM) and seeded on gelatin-coated plates at a split ratio of 1:3. DSFM will be changed every other day for 3-4 weeks. Cells are then subcultured using trypsinization, centrifuged, washed, and plated at 10,000 cells per cm$^2$ on gelatin-coated tissue culture plates in DSFM. To verify that epithelial monolayers are of ≥90% purity and express K14, cells are subjected to flow cytometry according to the method of Metallo et al (2010), *Methods Mol Biol* 585:83-92. To enhance the purity of isolated hEEPs, cells were sorted using magnetic activated cell sorting (MACS) with CD29 antibodies. About 92 percent of CD29 MACS sorted hEEP cell culture cells differentiated from eHLA-G(EF-1α)-GFP modified hESCs were positive for K14, a specific keratinocyte marker.

Genetically modified mammalian cells expressing transgenic eHLA-G, as described herein, have reduced immunogenicity relative to corresponding mammalian cells that do not express HLA-G. For example, immunogenicity may be reduced by at least about 5% to about 95%, relative to a corresponding cell type that does not express exogenous HLA-G, e.g., about 6%, 7%, 10%, 12%, 15%, 20%, 30%, 40%, 50%, 65%, 70%, 80%, 85%, 90%, or another percent reduced immunogenicity relative to cells of the same cell type that do not express exogenous HLA-G.

Methods for determining immunogenicity of cells are known in the art. For example, in some embodiments, HLA-G modified mammalian cells (e.g., human embryonic stem cells, or differentiated cells from HLA-G modified embryonic stem cells, or cells that are already fully differentiated prior to modification, etc.) or unmodified mammalian cells are cultured in the presence of an allogeneic natural killer cell line (e.g., NK-92) and then cytotoxicity to the HLA-G modified versus unmodified cells by induced by the NK-92 cells is determined by any of a number of standard cell viability assays.

Nucleic Acids Containing Enhanced HLA-G (eHLA-G) Transgene

The isolated nucleic acids (e.g., mammalian plasmid expression vectors) used to generate HLA-modified mammalian cells, as described herein, contain an enhanced HLA-G "eHLA-G" transgene that drives increased cell surface expression and/or secretion of HLA-G relative to cell surface expression driven by a wildtype HLA-G transgene. Such a transgene typically includes at least three distinct components: a promoter and 5' untranslated region (5' UTR) sequence; a coding sequence; and a 3' untranslated region (3' UTR) sequence.

In some embodiments, the promoter to be used to drive eHLA-G transgene expression is one capable of driving expression of the eHLA-G transgene in a cell type of interest for a period of at least about seven weeks to about 50 weeks, e.g., 8 weeks, 9 weeks, 10 weeks, 12 weeks, 15 weeks, 20 weeks, 25 weeks, 30 weeks, 35 weeks, 40 weeks, 42 weeks, 45 weeks, 47 weeks, 48 weeks, or another period from at least about seven weeks to about 50 weeks. Promoters capable of driving expression for such extended periods of time are effective in evading silencing that occurs in a number of cell types including, e.g., stem cells such as embryonic stem cells, induced pluripotent stem cells, or mesenchymal stem cells.

Suitable, silencing-resistant promoters include, but are not limited to, the Chinese hamster elongation factor-1 alpha (CHEF-1α) promoter (see Running Deer et al (2004), *Biotechnol. Prog.*, 20:880-889; and GenBank Accession No. AY188393.1), the M-U3/R-variant promoter of the Murine Stem Cell Virus (MSCV) promoter (as described in Swindle et al (2004), *J Biol Chem*, 279:34-41), the phosphoglycerate kinase (PGK) promoter, the human β-actin promoter, and the ubiquitin C promoter.

In some embodiments, the promoter used to drive expression of an eHLA-G transgene is expressed in one or more desired cell types at a level that is higher than in other cell types. One of ordinary skill in the art will appreciate that, for example, where an HLA-G modified stem is to be differentiated into a particular cell type, it may be advantageous to select a promoter that is active within or even selective for that particular cell type. For example, for a given tissue or cell type-selective promoter the expression level may be about two fold to 100 fold higher in the desired cell type compared to another cell type, e.g., about 3 fold, 4 fold, 5 fold, 10 fold, 20 fold, 25 fold, 30 fold, 40 fold, 50 fold, 70 fold, 80 fold, 90 fold, or another fold higher level of expression in the desired cell type compared to another cell type. Examples of tissue and/or cell type-selective promoters include, but are not limited to, the promoters for: Neuron-Specific Enolase (neuronal), Synapsin (neuronal), CamKII (forebrain neurons), HB9 (motor neurons), and Dopamine Transporter (dopaminergic neurons); Glial Fibrillary Acidic Protein (astrocytes); Albumin (liver); α-Myosin Heavy Chain (αMHC-cardiomyocytes); Neurogenin 3 and Pancreas-Duodenum Homeobox 1 (pancreas); Keratin 14 (skin); and Bestrophin1 (retinal pigment epithelium);

Typically the eHLA-G transgene sequence encodes an HLA-G protein that contains at least one to about ten point mutations relative to the human (GenBank No. NP_002118.1), or chimpanzee consensus sequence, e.g., 2, 3, 4, 5, 6, 7, 8, 9, or 10 point mutations relative to the above-mentioned HLA-G protein consensus sequences.

The human consensus wildtype sequence (SEQ ID NO:1) is shown below:

MVVMAPRTLFLLLSGALTLTETWAGSHSMRYFSAAVSRPGRGEPRFIA

MGYVDDTQFVRFDSDSACPRMEPRAPWVEQEGPEYWEEETRNTKAH

AQTDRMNLQTLRGYYNQSEASSHTLQWMIGCDLGSDGRLLRGYEQY

AYDGKDYLALNEDLRSWTAADTAAQISKRKCEAANVAEQRRAYLEGT

CVEWLHRYLENGKEMLQRADPPKTHVTHHPVFDYEATLRCWALGFY

PAEHLTWQRDGEDQTQDVELVETRPAGDGTFQKWAAVVVPSGEEQR

YTCHVQHEGLPEPLMLRWKQSSLPTIPIMGIVAGLVVLAAVVTGAAVA

AVLWRKKSSD

In some embodiments, the at least one to about ten point mutations increase the level of expression of the HLA-G protein on the cell surface of the expressing host cell by reducing retention of HLA-G in the endoplasmic reticulum during processing and maturation of the protein. Such mutations include, for example, an HLA-G "KK" motif mutation. See, e.g., Park et al (2001), *Immunity*, 15:213-224. In some cases the KK motif mutation includes a K334A mutation, a K335A mutation, or both substitution mutations. In other cases, the substitution may be made with a different aliphatic amino (e.g., leucine) acid or another type of amino acid that is non-basic.

In one example, the encoded HLA-G protein has the amino acid sequence of (SEQ ID NO:2), in which K334A and K335A substitutions, relative to the wildtype sequence, have been introduced (underlined):

MVVMAPRTLFLLLSGALTLTETWAGSHSMRYFSAAVSRPGRGEPRFIA

MGYVDDTQFVRFDSDSACPRMEPRAPWVEQEGPEYWEEETRNTKAHA

QTDRMNLQTLRGYYNQSEASSHTLQWMIGCDLGSDGRLLRGYEQYAY

DGKDYLALNEDLRSWTAADTAAQISKRKCEAANVAEQRRAYLEGTCV

EWLHRYLENGKEMLQRADPPKTHVTHHPVFDYEATLRCWALGFYPAE

IILTWQRDGEDQTQDVELVETRPAGDGTFQKVVAAVVVPSGEEQRYTCH

VQHEGLPEPLMLRWKQSSLPTIPIMGIVAGLVVLAAVVTGAAVAAVLW

R<u>AA</u>SSD

In some embodiments, an eHLA-G transgene encodes an HLA-G protein, the amino acid sequence of which is at least 75% to 100% identical to that of SEQ ID NO:2, e.g., 77%, 80%, 82%, 85%, 87%, 88%, 90%, 92%, 95%, 96%, 97%, 98%, 99%, or another percent identical to the amino acid sequence of SEQ ID NO:2.

The eHLA-G transgene disclosed herein also includes a 3' untranslated (3' UTR) region containing a number of regulatory elements affecting the expression/translational efficiency of HLA-G transcripts. In some embodiments the eHLA-G transgene 3' UTR sequence is a nucleic acid sequence that includes a nucleic acid sequence that is at least 75% identical to the sequence of (SEQ ID NO:3), e.g., at least 77%, 80%, 82%, 85%, 87%, 88%, 90%, 92%, 94%, 95%, 96%, 97%, or another percent identical to the sequence of HLA-G 3' UTR (SEQ ID NO:3):

TGTGAAACAGCTGCCCTGTGTGGGACTGAGTGGCAAGTCCCTTTGTG

ACTTCAAGAACCCTGACTTCTCTTTGTGCAGAGACCAGCCCA<u>A</u>CCCT

GTGCCCACCATGACCCTCTTCCTCATGCTGAACTGCATTCCTTCCCCA

ATCACCTTTCCTGTTCCAGAAAAGGGGCTGGGATGTCTCCGTCTCTG

TCTCAAATTTGTGGTCCACTGAGCTATAACTTACTTCTGTATTAAAAT

TAGAATCTGAGT<u>G</u>

Such sequences contain mutations (underlined) that decrease binding of two microRNA binding sites that result in increased expression of the trangene-encoded HLA-G. These sequences include a deletion of a 14 base pair sequence present in exon 8 of some HLA-G alleles. This 14 base pair sequence is shown below as SEQ ID NO NO:4:

14-bp insertion sequence in HLA 3' UTR
SEQ ID NO: 4
ATTTGTTCATGCCT

SEQ ID NO:5, shown below, corresponds to SEQ ID NO:3 with the insertion of this 14 base pair sequence (lower case):

(+14 BP HLA-G 3' UTR variant)
SEQ ID NO: 5
TGTGAAACAGCTGCCCTGTGTGGGACTGAGTGGCAAGatttgttcatgcc tTCCCTTTGTGACTTCAAGAACCCTGACTTCTCTTTGTGCAGAGACCAGC CCA<u>A</u>CCCTGTGCCCACCATGACCCTCTTCCTCATGCTGAACTGCATTCCT

TCCCCAATCACCTTTCCTGTTCCAGAAAAGGGGCTGGGATGTCTCCGT

CTCTGTCTCAAATTTGTGGTCCACTGAGCTATAACTTACTTCTGTATTA

AAATTAGAATCTGAGT<u>G</u>

Figure 13:
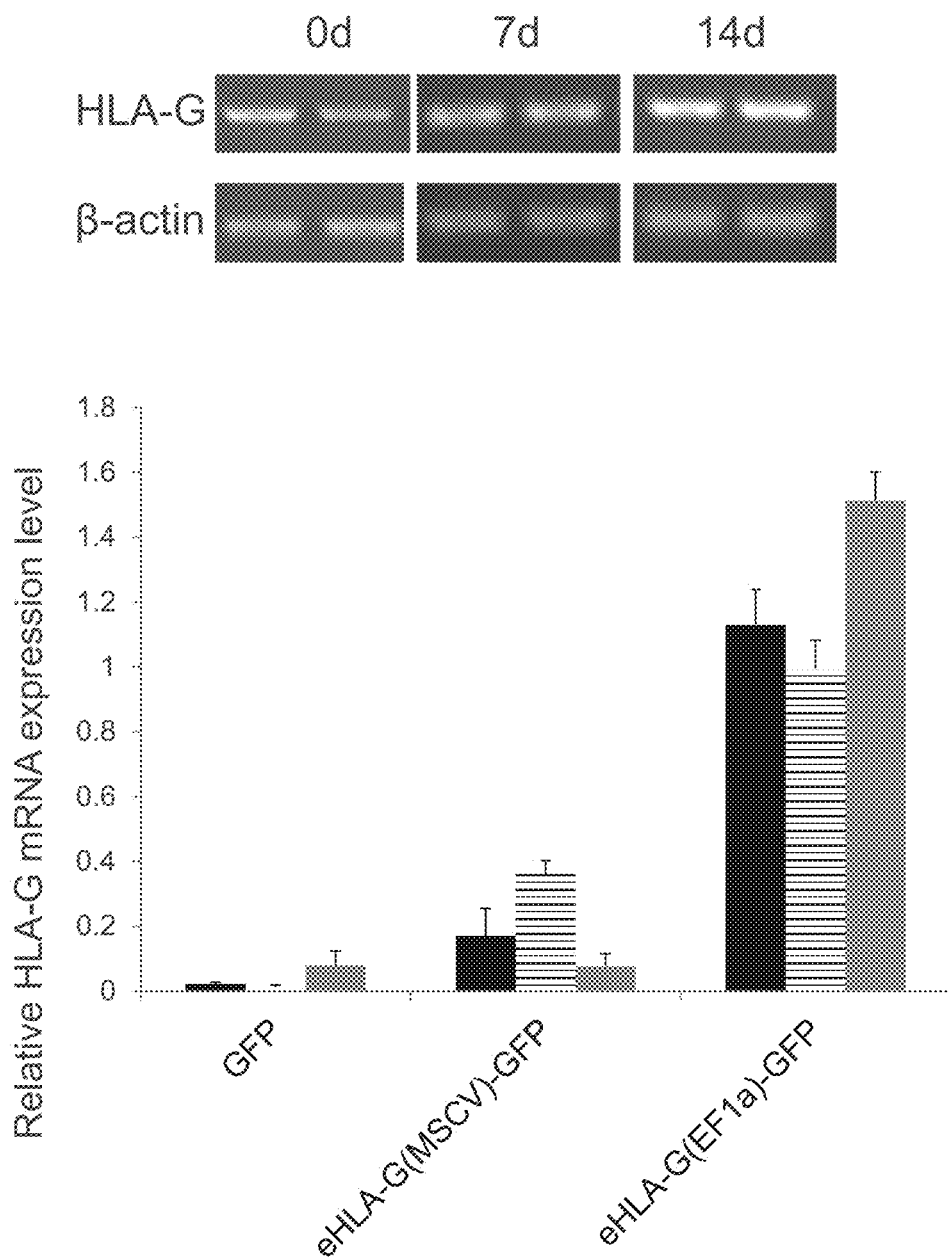
FIG. 13 (Top Panel) shows time course of eHLA-G transgene expression in an hESC line stably transfected with EF-1α promoter-driven expression of eHLA-G. (Bottom Panel) shows a comparison of the time course (black bars indicate at 0 days; horizontal striped bars indicate at 7 days; and grey bars indicate at 14 days) of HLA-G (mRNA) expression in a GFP-modified hESC line (negative control), an MSCV-promoter driven eHLA-G hESC line, and in an EF-1α driven eHLA-G hESC line. Note the higher and more persistent level of eHLA-G expression driven by the EF-1α promoter.

It has been reported that HLA-G alleles having a 3' UTR includes the above-mentioned 14 base insertion (see SEQ ID NO:4), yield a more stable HLA-G mRNA transcript. See Rouseau et al (2003), *Human Immunology*, 64:1005-1010. Surprisingly, as one basis for some embodiments of the instant disclosure, it was unexpectedly found that expression of the allele with a 14 base pair deletion (shown in SEQ ID NO:3) appeared to be more immunoprotective than the allele that includes the 14 pair insertion. See FIG. 13. While not wishing to be bound by theory, it is believed that the effect of the 14 bp deletion on expression levels of HLA-G may be cell type-specific, e.g., the 14 bp deletion apparently enhances expression of eHLA-G in human cells, including at least hESCs, hEEPs, and human dermal fibroblast cells.

In some embodiments, the nucleic acid sequence containing the eHLA-G transgene also includes insulator sequences that flank the eHLA-G expression cassette. Insulator sequences mitigate genomic position effects that could spuriously affect expression of an integrated exogenous expression cassette. In some embodiments, the insulator sequences to be used contain the chicken β-globin HS4 core insulator sequence.

In some embodiments, the nucleic acid containing the eHLA-G transgene will also include a selection marker as described herein. Optionally, the isolated nucleic acid containing the eHLA-G transgene may further contain a reporter protein as described herein.

In some embodiments, an eHLA-G-modified cell line is generated by the use of a transposon vector that comprises an eHLA-G expression cassette, but does not contain expression cassettes for a selection marker or a reporter protein. The vector is introduced to the cells to be modified along with a transposase expression vector, followed by limiting dilution cloning. As the population of cells transfected is very efficiently modified, the need to use selection markers or reporter proteins can be avoided. This is an important consideration, especially for cells to be used in the context of cell therapy in human patients. The percentage of cells that is successfully modified by transposon-based stable transfection methods can range from about 0.5% to about 50%, e.g., 1%, 2%, 3%, 5%, 7%, 8%, 15%, 20%, 22%, 30%, 40%, or another percentage from about 0.5% to about 50% of the cells transfected.

In some embodiments, expression of proteins encoded by a nucleic acid encoding two or more proteins is driven by separate promoters. In other embodiments, a polycistronic expression cassette may incorporate one or more internal ribosomal entry site (IRES) sequences between open reading frames incorporated into the polycistronic expression cassette. IRES sequences and their use are known in the art as exemplified in, e.g., Martinez-Salas (1999), *Curr Opin Biotechnol,* 10(5):458-464. Alternatively, multiple open reading frames may be linked to each other by an intervening 2A peptide sequence of the foot-and-mouth disease virus (F2A) or 2A-like sequences from other viruses. See, e.g., Hasegawa et al (2007), *Stem Cells,* 25:1707-1712 and Symczak et al (2004), *Nat Biotechnol,* 589-594. Inclusion of the 2A peptide sequence allows post-translational cleavage of a contiguous polypeptide containing eHLA-G and other sequences (e.g., a reporter protein sequence or a selection marker protein sequence) into separate proteins.

While identity between relatively short amino acid or nucleic acid sequences can be easily determined by visual inspection, analysis with an appropriate algorithm, typically facilitated through computer software, commonly is used to determine identity between longer sequences. When using a sequence comparison algorithm, test and reference sequences typically are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. A number of mathematical algorithms for rapidly obtaining the optimal alignment and calculating identity between two or more sequences are known and incorporated into a number of available software programs. Examples of such programs include the MATCH-BOX, MULTAIN, GCG, FASTA, and ROBUST programs for amino acid sequence analysis, and the SIM, GAP, NAP, LAP2, GAP2, and PIPMAKER programs for nucleotide sequences. Preferred software analysis programs for both amino acid and polynucleotide sequence analysis include the ALIGN, CLUSTALW (e.g., version 1.6 and later versions thereof), and BLAST programs (e.g., BLAST 2.1, BL2SEQ, and later versions thereof).

"Identity" (sometimes referred to as "overall identity"—in contrast to "local identity," which is discussed further herein) with respect to amino acid or nucleotide sequences refers to the percentage of amino acid residues or nucleotide bases, respectively, that are identical in the two amino acid or nucleotide sequences when two such amino acid sequences or two such nucleotide sequences are optimally aligned with one another. If, in the optimal alignment, a position in a first sequence is occupied by the same amino acid residue or nucleotide residue as the corresponding position in the second corresponding amino acid or nucleotide sequence, the sequences exhibit identity with respect to that residue position. The level of identity between two sequences (or "percent sequence identity") is measured as a ratio of the number of identical positions shared by the sequences with respect to the size of the sequences analyzed (i.e., percent sequence identity=(number of identical positions/total number of positions) times 100).

Also encompassed in the present disclosure are nucleic acids that hybridize specifically under low, medium, or high stringency conditions to a probe of at least 100 nucleotides from a nucleic acid encoding the amino acid sequence of SEQ ID NO:2 or to the nucleic acid sequence of SEQ ID NOS:3 or 5.

Low stringency hybridization conditions, as used herein, include, e.g., hybridization with a 100 nucleotide probe of about 40% to about 70% GC content; at 42° C. in 2×SSC and 0.1% SDS. Medium stringency hybridization conditions include, e.g., at 50° C. in 0.5×SSC and 0.1% SDS. High stringency hybridization conditions include, e.g., hybridization with the above-mentioned probe at 65° C. in 0.2×SSC and 0.1% SDS. Under these conditions, as the hybridization temperature is elevated, a nucleic acid with a higher sequence homology is obtained.

Compositions Comprising eHLA-G Genetically Modified Cells

Also encompassed herein are pharmaceutical compositions, topical compositions, cellular grafts, and artificial tissues comprising or generated using one or more HLA-G modified mammalian cell types. As shown herein, eHLA-G modified hESCs displayed stable and persistent HLA-G expression, even through directed differentiation into hEEPs. Furthermore, the stable and persistent HLA-G expression provided the genetically modified cells with reduced immunogenicity and/or improved immunosuppression. In addition, it is shown herein that eHLA-G modified human dermal fibroblasts, which are fully differentiated cells, also have stable and persistent HLA-G expression that provides reduced immunogenicity and/or improved immunosuppression. Thus, the eHLA-G constructs described herein can be used to generate universal donor cells of any type, whether from directed differentiation of a genetically modified pluripotent or multipotent cell, or from genetic modification of a fully differentiated cell.

In one aspect, a topical composition for skin regeneration or repair is provided that comprises a genetically modified dermal fibroblast cell comprising an eHLA-G transgene as described herein. In another aspect, a pharmaceutical composition for injection is provided that comprises a genetically modified dermal fibroblast cell comprising an eHLA-G transgene as described herein. In another aspect, a skin graft composition is provided that comprises a genetically modified dermal fibroblast cell comprising an eHLA-G transgene as described herein. In another aspect, a permanent skin graft composition is provided that comprises a genetically modified embryonic epidermal progenitor cell comprising an eHLA-G transgene as described herein.

In another aspect, biocompatible synthetic scaffolds for artificial tissue and methods for their generation are described in the art and may be used with the HLA-G modified cells described herein to produce an artificial tissue having reduced immunogenicity and/or improved immunosuppression as compared to tissues containing cells that do not express exogenous HLA-G. See, e.g., U.S. Pat. No. 7,960,166 entitled "Microfabricated compositions and processes for engineering tissues containing multiple cell types."

II. Methods
Cell Therapy Treatment

Because cells modified to stably express exogenous HLA-G in the manner described herein have reduced immunogenicity and/or increased immunosuppression, these traits allow the modified cell to serve as a universal or improved donor cell or tissue. This is because the HLA-G mediated reduction of immunogenicity and/or improvement in immunosuppression provided to the cell can reduce or eliminate the requirement of matching the type of classical human leukocyte antigen (HLA) class I and class II molecules between donor cells and the recipient) for numerous injuries, diseases, or disorders.

Thus, HLA-G modified cells that stably express eHLA-G (and optionally in addition, exogenous human β2 microglobulin), as described herein, may be used as for therapy. The therapy may be directed at treating the cause of the disease; or alternatively, the therapy may be to treat the effects of the disease or condition. The genetically modified cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair, including skin regeneration or skin repair.

In various embodiments, HLA-G modified mammalian cells (e.g., human HLA-G modified cells) are administered to a subject suffering from any of a number of conditions including, but not limited to cardiovascular disease, eye disease (e.g., macular degeneration), auditory disease, (e.g., deafness), diabetes, neurodegenerative disease, Alzheimer's Disease, Parkinson's Disease, multiple sclerosis, osteoporosis, liver disease, kidney disease, autoimmune disease, arthritis, gum disease, a dental condition, or a proliferative disorder (e.g., a cancer). In other cases, the subject is suffering from, or at high risk of suffering from, an acute health condition, e.g., stroke, spinal cord injury, burn, or a wound. In other cases, the subject is suffering from loss of tissue such as lipatrophy or aging-related losses in collagen. In other cases, the subject suffers from a non-healing ulcer, or is in need for an agent to assist in closure of defects like hypospadias and epispadias. In other cases, the subject is need for a permanent or temporary skin graft for wound healing or for skin substitutes.

In one aspect, the invention provides a universal method of cellular or tissue grafting to a subject in need thereof, the method comprising injecting or grafting to the subject a cellular or tissue composition comprising a population of eHLA-G modified cells, wherein the subject has at least one mismatched classical HLA class I or HLA class II molecule as compared to the population of eHLA-G modified cells, and wherein the population of eHLA-G modified cells exhibits reduced immunogenicity and/or improved immunosuppression as compared to cells of the same-type without the eHLA-G modification. The reduced immunogenicity and/or improved immunosuppression can be determined, for example, by comparing the eHLA-G modified cell to a control cell of the same type without the eHLA-G modification in an NK-92 cytotoxicity assay, a humanized NSG tumor growth assay, and/or a PBMC proliferation assay.

In another aspect, the invention provides a method for regenerating skin to a subject in need thereof, the method comprising injecting a population of eHLA-G modified dermal fibroblasts and/or eHLA-G modified embryonic epidermal progenitors to a site of skin injury on the subject, wherein the subject has at least one mismatched classical HLA class I or HLA class II molecule as compared to the population of eHLA-G modified dermal fibroblasts and/or eHLA-G modified embryonic epidermal progenitors.

HLA-G modified cell types to be administered to a subject in need thereof include, but are not limited to, epidermal progenitor cells, mesenchymal stem cells, pancreatic β cell progenitors, pancreatic β cells, cardiac progenitors, cardiomyocytes, hepatic progenitors, hepatocytes, muscle cell progenitors, muscle cells, kidney cells, osteoblasts, hematopoietic progenitors, dental follicle cells, hair follicle cells, retinal pigment epithelial cells, neural stem cells, neurons, astrocytes, oligodendrocytes, or any combination thereof. Such mammalian cells can be derived from one of several species including, e.g., human, mouse, rat, monkey, or pig.

The therapy may be directed at treating the cause of the disease; or alternatively, the therapy may be to treat the effects of the disease or condition. The HLA-G modified cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from HLA-G modified pluripotent (or totipotent) stem cells. The transferred cells also may be multipotent stem cells differentiated from pluripotent, HLA-G modified cells.

The number of administrations of treatment to a subject may vary. Introducing the HLA-G modified and/or differentiated cells into the subject may be a one-time event; but in certain situations, such treatment may elicit improvement for a limited period of time and require an on-going series of repeated treatments. In other situations, multiple administrations of the cells may be required before an effect is observed. As will be appreciated by those of ordinary skill in the art, the exact treatment protocols will depend upon the disease or condition, and the stage of the disease and parameters of the individual subject being treated.

The HLA-G modified cells may be introduced to the subject via any of the following routes: parenteral, intravenous, intraarterial, intramuscular, subcutaneous, transdermal, intratracheal, intraperitoneal, or into spinal fluid.

The HLA-G modified cells may be differentiated into cells and then transferred to subjects suffering from a wide range of diseases or disorders.

Pancreatic islet cells (or primary cells of the islets of Langerhans) may be transplanted into a subject suffering from diabetes (e.g., diabetes mellitus, type 1), see e.g., Burns et al., (2006) *Curr. Stem Cell Res. Ther.*, 2:255-266. Thus, in some embodiments, pancreatic beta cells derived from HLA-G modified cells are transplanted into a subject suffering from diabetes (e.g., diabetes mellitus, type 1).

In other examples, hepatic cells or hepatic stem cells derived from HLA-G modified cells are transplanted into a subject suffering from a liver disease, e.g., hepatitis, cirrhosis, or liver failure.

Degenerative heart diseases such as ischemic cardiomyopathy, conduction disease, and congenital defects could benefit from stem cell therapies. See, e.g., Janssens et al., (2006), *Lancet*, 367:113-121.

Hematopoietic cells or hematopoietic stem cells (HSCs) derived from HLA-G modified cells may be transplanted into a subject suffering from cancer of the blood, or other blood or immune disorder. Examples of cancers of the blood that are potentially treated by hematopoietic cells or HSCs include: acute lymphoblastic leukemia, acute myeloblastic leukemia, chronic myelogenous leukemia (CML), Hodgkin's disease, multiple myeloma, and non-Hodgkin's lymphoma. Often, a subject suffering from such disease must undergo radiation and/or chemotherapeutic treatment in order to kill rapidly dividing blood cells. Introducing HSCs derived from HLA-G modified cells to these subjects may help to repopulate depleted reservoirs of cells.

Subjects suffering from neurological diseases or disorders could especially benefit from HLA-G modified cell therapy, especially when the blood/brain barrier may have been compromised. In some approaches, the HLA-G modified cells may be differentiated into neural stem cells or neurons and then transplanted to an injured site to treat a neurological condition, e.g., Alzheimer's disease, Parkinson's disease, multiple sclerosis, cerebral infarction, spinal cord injury, or other central nervous system disorder, see, e.g., Morizane et al., (2008), *Cell Tissue Res.*, 331(1):323-326; Coutts and Keirstead (2008), *Exp. Neurol.*, 209(2):368-377; Goswami and Rao (2007), *Drugs*, 10(10):713-719.

For the treatment of Parkinson's disease, the HLA-G modified cells may be differentiated into dopamine-acting neurons and then transplanted into the striate body of a subject with Parkinson's disease. For the treatment of multiple sclerosis, neural stem cells may be differentiated into oligodendrocytes or progenitors of oligodendrocytes, which are then transferred to a subject suffering from MS.

For the treatment of any neurologic disease or disorder, a successful approach may be to introduce neural stem cells to the subject. For example, in order to treat Alzheimer's disease, cerebral infarction or a spinal injury, the HLA-G modified cells may be differentiated into neural stem cells followed by transplantation into the injured site. The HLA-G modified cells may also be engineered to respond to cues that can target their migration into lesions for brain and spinal cord repair, e.g., Chen et al., (2007), *Stem Cell Rev.*, 3(4):280-288.

Optionally, the HLA-G modified cells to be used in cell therapy methods also express a reporter protein as described herein. In some embodiments, the reporter protein to be used is one that facilitates in vivo detection (e.g., imaging) of the introduced cells. For example, the cells may express a far-red emitting fluorescent protein such as Katushka, whose long excitation and emission wavelengths are well suited to imaging in tissues. Katushka is commercially available under the tradename "TurboFP635" (Evrogen, Moscow, Russia).

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1 Identification of Gene Expression Patterns Associated with Immune Tolerance of Cancer Cells Human soft tissue cancer arrays were initially screened in search of a candidate immune tolerance gene that showed increased expression with cancer progression to metastatic states, presumably due to evasion of immune surveillance mechanisms. The data revealed a strong positive correlation between successful metastasis and expression levels of several genes previously implicated in the immune tolerance. To assess whether MSCs could induce immune tolerance and allograft acceptance, MSCs were cross-screened by RT-PCR to examine the expression levels of these candidate genes and several antigenic HLAs. Table 1 illustrates that passage 1 MSCs expressed HLA class Ia, HLA-G and II markers in addition to CD200, CD47, and indoleamine 2,3-dioxygenase (IDO). It was found that a population of MSCs expressed HLA-G at moderate levels, albeit less than that found for Jeg-3, a cancer line with aggressive metastatic potential.

TABLE 1

| Cell type | Passage # | HLA class Ia | HLA-G | HLA class II | IDO | CD200 | CD47 |
| --- | --- | --- | --- | --- | --- | --- | --- |
| MSC G⁻ | 1 | ++++ | − | −/+ | + | ++ | + |
|  | 3 | ++++ | − | ++ | + | ++ | + |
| MSC G⁺ | 1 | ++++ | ++ | −/+ | + | ++ | + |
|  | 3 | ++++ | − | ++ | + | ++ | + |
| Jeg3 | 1 | ++ | +++ | −/+ | − | − | + |
|  | 3 | ++ | +++ | −/+ | − | − | + |

Since the immunosuppressive effect of MSCs in vivo appears to be transient, MSCs were serially passaged and monitored for changes in the expression levels of the selected genes. By passage 3, native HLA-G expression was absent in MSCs, although other candidate markers remained unchanged. HLA-G expression was not altered in Jeg-3 cells. MSCs were then isolated based on expression of cell surface HLA-G using FACS and found that between 0.5-3% of MSCs expressed HLA-G at the cell surface. To assess the ability of HLA-G⁺ MSCs to escape donor rejection in vivo, 1-3×10⁵ cells were injected into the tail veins of immunocompetent mice. Blood samples (200 µl) were collected from the retro-orbital plexus and FACS sorted using an anti-human HLA class I specific mAb. Table 2 shows that 1 week post-transplantation, HLA-G+ MSCs (and Jeg-3 cells) demonstrated a 24- and 270-fold survival advantage over HSCs and Jurkat cells (both HLA-G⁻), respectively. By two weeks, the advantage of HLA-G⁺ MSCs increased to 27-and 311-fold. HLA-G⁻ MSCs survived at the same rate as HSCs, suggesting that the HLA-G⁺ subpopulation of MSCs may exhibit enhanced tolerizing effects relative to unsorted MSCs in an in vivo setting. Indeed, post-mortem analysis revealed frank tumors in the lungs of immunocompetent mice 12 weeks post-transplantation with Jeg-3 cells, but not G⁺ MSCs (data not shown).

TABLE 2

| Cell Type | HLA-G | Sampling Time | % Survival |
| --- | --- | --- | --- |
| 100k MSCs | − | 2 weeks | 0.51% |
| 100k MSCs | + | 1 week | 10.82% |
|  |  | 2 weeks | 12.47% |
| 150k Jeg-3 | + | 1 week | 13.5% |

TABLE 2-continued

| Cell Type | HLA-G | Sampling Time | % Survival |
|---|---|---|---|
| 300k HSCs | – | 1 week | 0.46% |
| 300k Jurkat | – | 1 week | 0.04% |

Next, a modified HLA-G construct was overexpressed in HF (human fibroblast) and K562 cells and tested for protection against lysis by human NK cells (Table 3). NK-mediated cytotoxicity was reduced by 75% in HLA-G$^+$ HF and virtually eliminated in HLA-G+ K562 cells. This is consistent with the observed protection of HLA-G$^+$ Jeg-3, which was reversed by incubation with the neutralizing anti-HLA-G (87G) antibody but not an isotype control. These data suggest that protection from NK killing was HLA-G-dependent.

TABLE 3

| Promoter | ER Retrieval | 3' UTR | HLA-G Surface Exp | Cytotoxic Lysis (3:1) | Silencing |
|---|---|---|---|---|---|
| pMSCV | wildtype | absent | low-medium | 32-41% | 4-6 weeks |
| pMSCV | wildtype | wildtype | low | 40-60% | 4-6 weeks |
| pMSCV | mutated | wildtype | medium | 25-33% | 4-6 weeks |
| pMSCV$^{mut}$ | wildtype | absent | low-medium | 35-42% | None @ 12 mo |
| pMSCV$^{mut}$ | mutated | mutated | high | 0-8% | None @ 5 mo |

Previous studies showed that the mutated MSCV promoter, M-U3/R, avoided silencing pressure through 10 weeks of culture. Our studies showed that M-U3/R resisted silencing after 1 year of continuous culture, superior to the wildtype promoter which was silenced by 4-6 weeks of culture. Moreover, mutation or deletion of the 3' UTR enhanced HLA-G surface expression, as did mutation of the ER retrieval motif. Higher HLA-G surface expression negatively correlated with cytotoxic lysis, reinforcing the importance of employing an optimal gene delivery construct.

Example 2 Culture and Differentiation of Human Embryonic Stem Cells into Human Epidermal Progenitors (hEEPs)

All tissue culture reagents were from Life Technologies unless otherwise specified. ESC growth medium contains DMEM/F12 (1:1) supplemented with 20% knockout serum replacement, 0.1 mM MEM non-essential amino acids, 1 mM GlutaMax, 0.1 mM β-mercaptoethanol (Sigma). ESC growth medium was conditioned by plating mitotically inactivated mouse embryonic fibroblasts (MEFs) (CF-1, ATCC) at a density of 5×10$^4$ cells/cm$^2$ and incubating for 18-24 hours. After conditioning, 4 ng/ml bFGF was added and complete conditioned medium was sterile filtered. hESCs were subcultivated every 5-6 days (1:3 or 1:4 split) on Matrigel-coated plates using 1 mg/ml Dispase to remove cell colonies. K14$^+$/p63$^+$ hEEPs were generated according to the method of Metallo et al supra. Briefly, hESCs were cultured in 6-well plates for 4 days and then treated with 2 ml/well of differentiation medium, comprised of unconditioned hESC growth medium containing 1 µM all-trans retinoic acid (Sigma) and 25 ng/ml BMP4. After daily medium changes for 7 days, cells were treated with dispase, centrifuged, and resuspended in defined keratinocyte serum-free medium (DFSM) and seeded on gelatin-coated plates at a split ratio of 1:3. DSFM was changed every other day for 3-4 weeks. Cells were then subcultured by trypsinization, centrifuged, washed, and plated at 10,000 cells per cm$^2$ on gelatin-coated tissue culture plates in DSFM. After 14 days in defined keratinocyte serum-free medium, early signs of epidermal differentiation was observed by microscopy as characterized by the formation of an epidermal sheet structure. After four weeks of culturing, cells in epidermal sheets displayed typical epidermal differentiation phenotype with cubic morphology.

Figure 12:
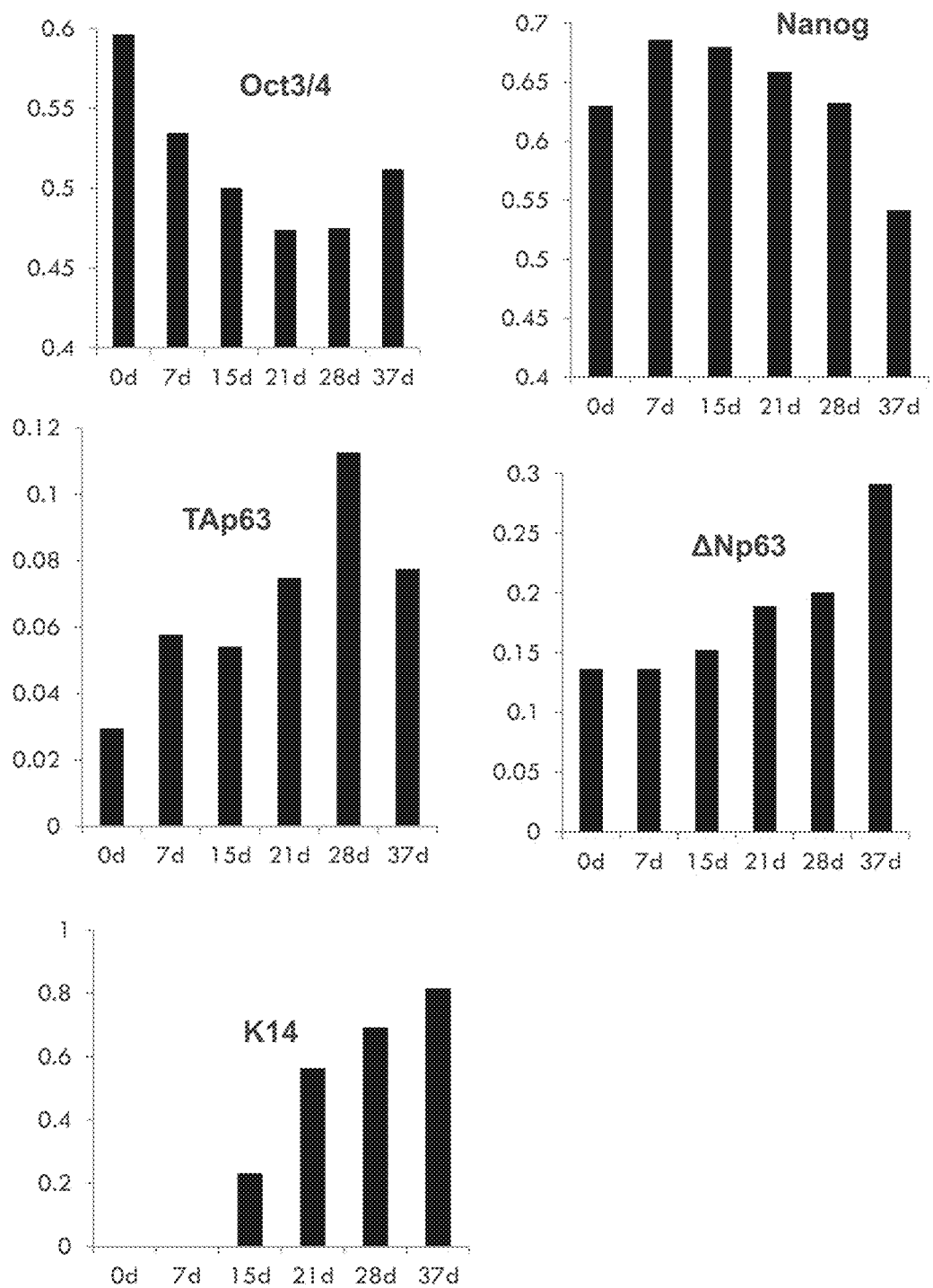
FIG. 12 shows a series of bar graphs depicting the time course of gene expression levels of several pluripotency markers and epidermal progenitor markers during directed differentiation of hESCs in vitro into embryonic epidermal progenitors (EEPs). The y-axis values are relative mRNA expression levels as determined by semi-quantitative RT-PCR. The x-axis values are the days at which expression was assessed. See Example 2 for further description. The FIG. 12 data indicates that the epidermal differentiation markers K14, Tap63, and ΔNp63 were gradually enhanced during differentiation. In data not shown here, immunofluorescence studies of K14 and additional epidermal markers p63, CD29, and CD49f were conducted. Differentiated eHLA-G(EF-1a)-GFP hEEPs were positive for K14, p63, CD29, and CD49f protein expression as indicated by immunofluorescence.

Isolation of total RNA from cells and reverse transcriptase reactions were described previously in Zhao et al (2010), Tissue Eng Part A, 16(2):725-733. Specific PCR amplification was performed in the Hybaid Omnigene thermal cycler (Bio-rad, Hercules, Calif.) using specific primers of the genes of interest as shown in FIG. 12. PCR conditions consisted of 35 cycles at 94° C. for 30 s, 65° C. for 1 min, and 72° C. for 1 min with a final extension at 72° C. for 10 min. Ten pi of each PCR product was detected by ethidium bromide gel electrophoresis. The FIG. 12 data indicates that the epidermal differentiation markers K14, Tap63, and ΔNp63 were gradually enhanced during differentiation. In data not shown here, immunofluorescence studies of K14 and additional epidermal markers p63, CD29, and CD49f were conducted. Differentiated eHLA-G(EF-1α)-GFP hEEPs were positive for K14, p63, CD29, and CD49f protein expression as indicated by immunofluorescence.

Figure 16:
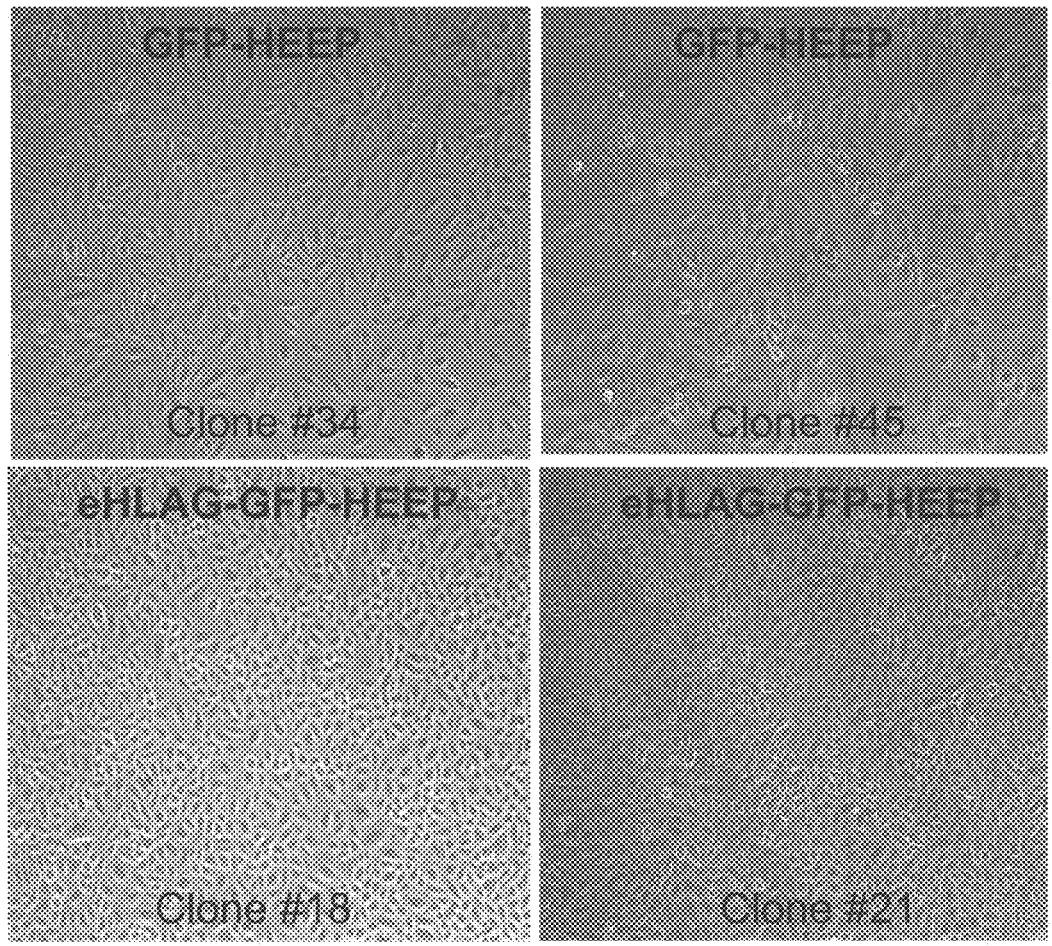
FIG. 16. Purified hEEPs exhibited homologous keratinocyte morphology as shown by phase contrast microscopy. eHLA-G-GFP-hEEP clones 18 and 21 were differentiated from modified eHLA-G(EF-1α)-GFP-hESCs as described in Example 2.

To verify that epithelial monolayers were of ≥90% purity and express K14, cells were subjected to flow cytometry according to the method of Metallo et al supra, and analyzed on a BD FACS Canto II. The impact of eHLA-G transgene expression (eHLA-G(EF1-α)-GFP-hESCs) on hESC differentiation into EPs (epidermal progenitors) was assessed by comparing the degree of K14 positivity for wildtype, G$^-$, and G$^+$-hEEPs. To enhance purity of isolated hEEPs, cells were sorted using magnetic activated cell sorting (MACS) with CD29 antibodies. About 92 percent of CD29 MACS sorted hEEP cell culture cells differentiated from eHLA-G (EF-1α)-GFP modified hESCs were positive for K14, a specific keratinocyte marker. Purified hEEPs exhibited homologous keratinocyte morphology as shown by phase contrast microscopy (see FIG. 16).

Figure 17:
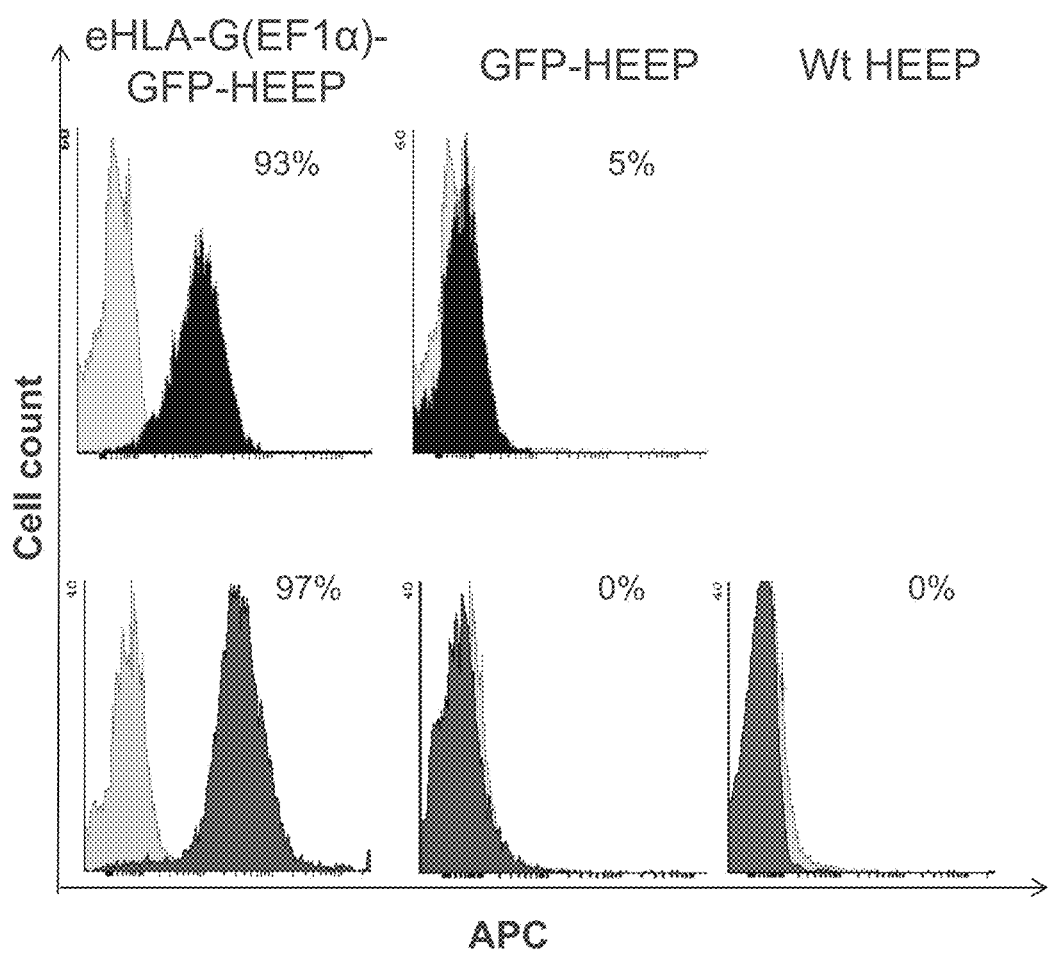
FIG. 17. The stability of the HLA-G transgene in differentiated hEEPs was confirmed by flow cytometry. Both HLA-G total expression (top panels) and surface expression (bottom panels) was robust for differentiated eHLA-G(EF-1a)-GFP-hEEPs (greater than 90% of cells) as compared to control cells with no exogenous HLA-G (GFP only hEEPs) and wild-type hEEPs.

The stability of the HLA-G transgene in differentiated hEEPs was confirmed by flow cytometry. Both HLA-G total expression and surface expression was robust for differentiated eHLA-G(EF-1α)-GFP-hEEPs (greater than 90% of cells) as compared to control cells with no exogenous HLA-G (GFP only hEEPs) and wild-type hEEPs (see FIG. 17). Only clones that yield a similar differentiation potential as wildtype cells were selected for further study.

Example 3 eHLA-G Construct Design and Stable Expression in hESCs

A novel HLA-G construct was designed by combining multiple modifications: 1) mutation of HLA-G's ER retrieval motif (K334A/K335A); and 2) mutation of HLA-G's 3' UTR microRNA binding sites. Since viral gene delivery systems remain a serious regulatory challenge, the PiggyBac system was used, a transposon-based, nonviral approach that was recently shown to achieve a 90% transfection efficiency in H1 hESCs (Lacoste et al (2009), Cell Stem Cell, 5:332-342.). This system requires a donor plasmid containing the transposon (FIG. 1A) and a helper plasmid expressing the transposase (FIG. 2). To generate helper plasmids, the ePiggyBac codon humanized transposase cDNA was custom synthesized (GeneArt) and then cloned in pBluescript (Stratagene) downstream of a PGK promoter and upstream of an SV40 polyadenylation signal sequence (pA). For the eHLA-G expression cassette, multiple promoters were compared including the M-U3/R promoter, MSCV promoter, and the Chinese hamster EF1α (CHEF-1α) promoter, the sequence of which is provided below as SEQ ID NO:6.

one embodiment of the CHEF-1α promoter
(SEQ ID NO: 6)
GGATGGCGGGGCTGACGTCGGGAGGTGGCCTCCACGGGAAGGGACACCCG

GATCTCGACACAGCCTTGGCAGTGGAGTCAGGAAGGGTAGGACAGATTCT

GGACGCCCTCTTGGCCAGTCCTCACCGCCCCACCCCCGATGGAGCCGAGA

GTAATTCATACAAAAGGAGGGATCGCCTTCGCCCCTGGGAATCCCAGGGA

CCGTCGCTAAATTCTGGCCGGCCTCCCAGCCCGGAACCGCTGTGCCCGCC

CAGCGCGGCGGGAGGAGCCTGCGCCTAGGGCGGATCGCGGGTCGGCGGGA

GAGCACAAGCCCACAGTCCCCGGCGGTGGGGAGGGGCGCGCTGAGCGGG

GGCCCGGGAGCCAGCGCGGGCAAACTGGGAAAGTGGTGTCGTGTGCTGG

CTCCGCCCTCTTCCCGAGGGTGGGGAGAACGGTATAAAAGTGCGGTAGT

CGCGTTGGACGTTCTTTTTCGCAACGGGTTTGCCGTCAGAACGCAGGTGA

GTGGCGGGTGTGGCCTCCGCGGGCCCGGGCTCCCTCCTTTGAGCGGGGTC

GGACCGCCGTGCGGGTGTCGTCGGCCGGGCTTCTCTGCGAGCGTTCCCGC

CCTGGATGGCGGGCTGTGCGGGAGGGCGAGGGGGGGAGGCCTGGCGGCGG

CCCCGGAGCCTCGCCTCGTGTCGGGCGTGAGGCCTAGCGTGGCTTCCGCC

CCGCCGCGTGCCACCGCGGCCGCGCTTTGCTGTCTGCCCGGCTGCCCTCG

ATTGCCTGCCCGCGGCCCGGGCCAACAAAGGGAGGGCGTGGAGCTGGCTG

GTAGGGAGCCCCGTAGTCCGCATGTCGGGCAGGGAGAGCGGCAGCAGTCG

GGGGGGGGACCGGGCCCGCCCGTCCCGCAGCACATGTCCGACGCCGCCTG

GACGGGTAGCGGCCTGTGTCCTGATAAGGCGGCCGGGCGGTGGGTTTTAG

ATGCCGGGTTCAGGTGGCCCCGGGTCCCGGCCCGGTCTGGCCAGTACCCC

GTAGTGGCTTAGCTCCGAGGAGGGCGAGCCCGCCCGCCCGGCACCAGTTG

CGTGCGCGGAAAGATGGCCGCTCCCGGGCCCTGTAGCAAGGAGCTCAAAA

TGGAGGACGCGGCAGCCCGGCGGAGCGGGGCGGGTGAGTCACCCACACAA

AGGAAGAGGGCCTTGCCCCTCGCCGGCCGCTGCTTCCTGTGACCCCGTGG

TGTACCGGCCGCACTTCAGTCACCCCGGGCGCTCTTTCGGAGCACCGCTG

GCCTCCGCTGGGGAGGGGATCTGTCTAATGGCGTTGGAGTTTGCTCACA

TTTGGTGGGTGGAGACTGTAGCCAGGCCAGCCTGGCCATGGAAGTAATTC

TTGGAATTTGCCCATTTTGAGTTTGGAGCGAAGCTGATTGACAAAGCTGC

TTAGCCGTTCAAAGGTATTCTTCGAACTTTTTTTTAAGGTGTTGTGAAA

ACCACCG

To generate the donor plasmid, T53C/C136T mutant 5' terminal repeat (TR) of 313 bp and 3' TR of 235 bp (as described in Lacoste supra) were custom synthesized and cloned upstream and downstream, respectively, of the following expression cassette: eHLA-G, a 250 bp chicken β-globin HS4 core insulator (Recillas-Targa et al (2002), PNAS USA, 99:6883-6888), EGFP, and pA. HS4 was used to prevent spreading of repressive chromatin into the integrated construct. EGFP expression was driven by the phosphoglycerate kinase (PGK) promoter (see FIG. 1A). The sequence of the HS4 element is shown below as SEQ ID NO:7.

one embodiment of the HS4 element
(SEQ ID NO: 7)
GAGCTCACGGGGACAGCCCCCCCCCAAAGCCCCCAGGGATGTAATTACGT

CCCTCCCCCGCTAGGGGGCAGCAGCGAGCCGCCCGGGGCTCCGCTCCGGT

CCGGCGCTCCCCCCGCATCCCCGAGCCGGCAGCGTGCGGGGACAGCCCGG

GCACGGGGAAGGTGGCACGGGATCGCTTTCCTCTGAACGCTTCTCGCTGC

TCTTTGAGCCTGCAGACACCTGGGGGATACGGGGAAAAAGCTT

Figure 1:
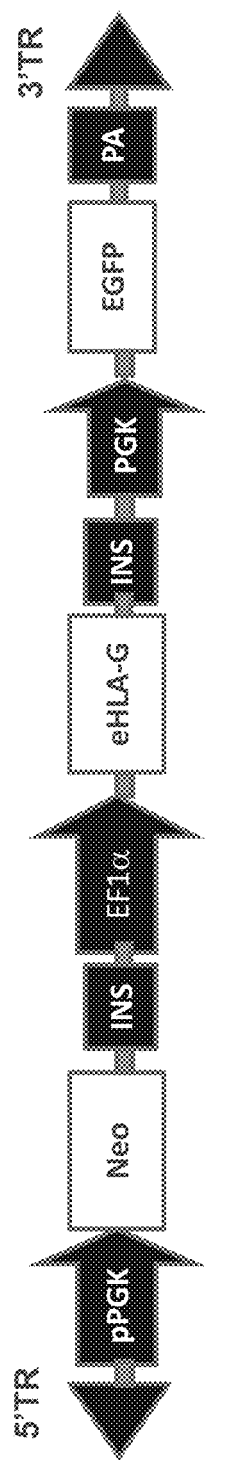
FIG. 1 shows a schematic depiction of a non-limiting embodiment of an enhanced HLA-G (eHLA-G) transgene expression transposon vector containing a selection marker (neomycin phosphotransferase) driven by a phosphoglycerate kinase (PGK) promoter; "INS" flanking insulator elements; a Chinese Hamster EF-1α promoter driving expression of eHLA-G; a PGK promoter driving expression of EGFP; and 5' terminal repeat (TR) transposition elements. An eHLA-G transgene contains a combination of mutations and/or non-coding elements (such as, for example, a promoter or modified 3' UTR) that enhance expression, particularly cell surface expression, of the HLA-G protein. For the experiments described herein, the eHLA-G transgene comprised the above elements, and more specifically included a human HLA-G coding sequence as listed in SEQ ID NO:2 with 1) mutations of HLA-G's ER retrieval motif (K334A/K335A); and 2) mutation of HLA-G's 3' UTR microRNA binding sites, wherein this modified 3' UTR had the sequence as listed in SEQ ID NO:3. See Example 3 for further description.
Figure 2:
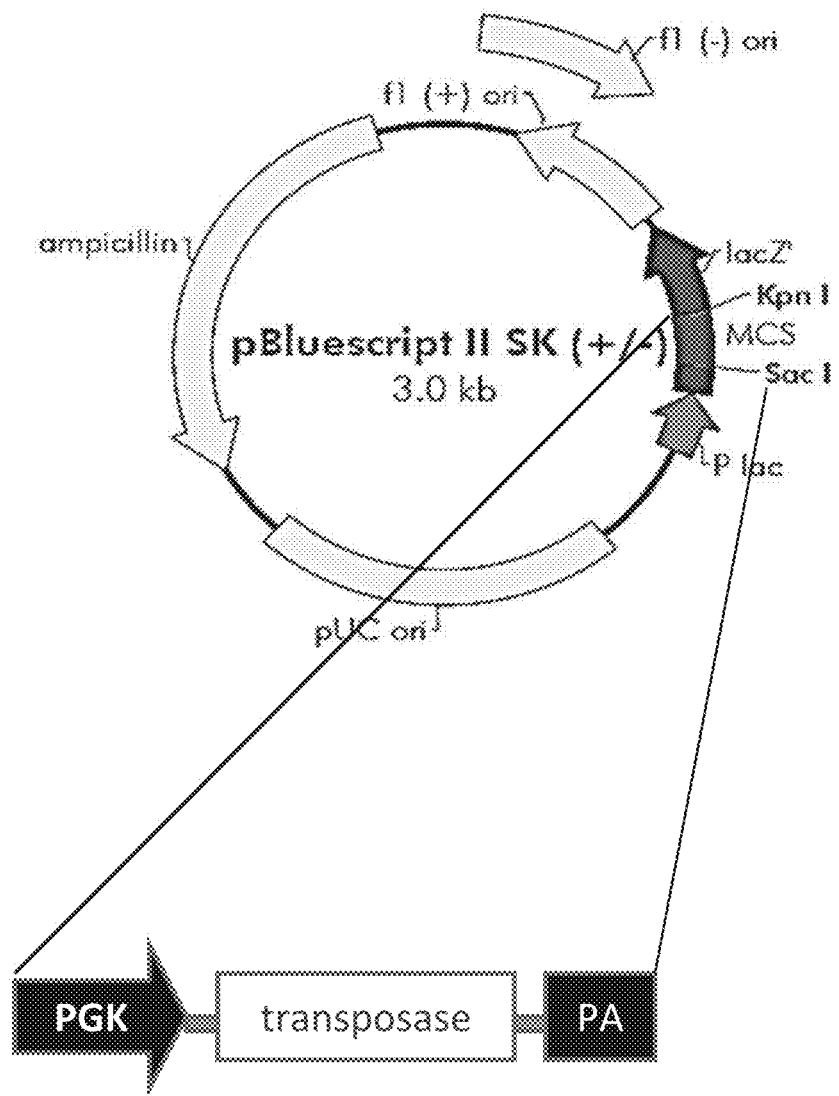
FIG. 2 shows a schematic depiction of a non-limiting embodiment of a transposase expression helper vector used to drive genomic integration of a co-transfected transposon expression vector.

The empty vector donor plasmid (HLA-G⁻) was identical to the eHLA-G donor plasmid except that the eHLA-G construct was excluded (FIG. 1B). Prior to gene transfer, hESCs were treated for 1 hr with 10 µM Y-27632, a ROCK inhibitor shown to substantially reduce dissociation-induced apoptosis and increases cloning efficiency (Watanabe et al (2007), Nat Biotechnol, 25:681-686. hESCs were dissociated in 0.25% trypsin-EDTA at 37° C. for five minutes, washed in conditioned mTeSR medium plus Y-27632, and resuspended in nucleofection solution L (Amaxa). 3 µg of helper and 6 µg of transposon donor plasmids were added per $1.5 \times 10^5$ cells, and nucleofection was performed with program setting B-016. hESCs were then plated in CM plus Y-27632 at $2 \times 10^5$ cells per 6 cm dish for clonal selection. After 24 hours, the culture medium was changed to CM alone, then changed daily thereafter. Clones with the highest dual expression of tdT/eHLA-G were selected using fluorescence microscopy rather than via antibiotic resistance or flow cytometry since transgene silencing is frequent in hESCs and only a fraction of single transgenic cells gives rise to a marked cell line (Braam et al (2008), Nat Methods, 5:389-392).

Figure 3:
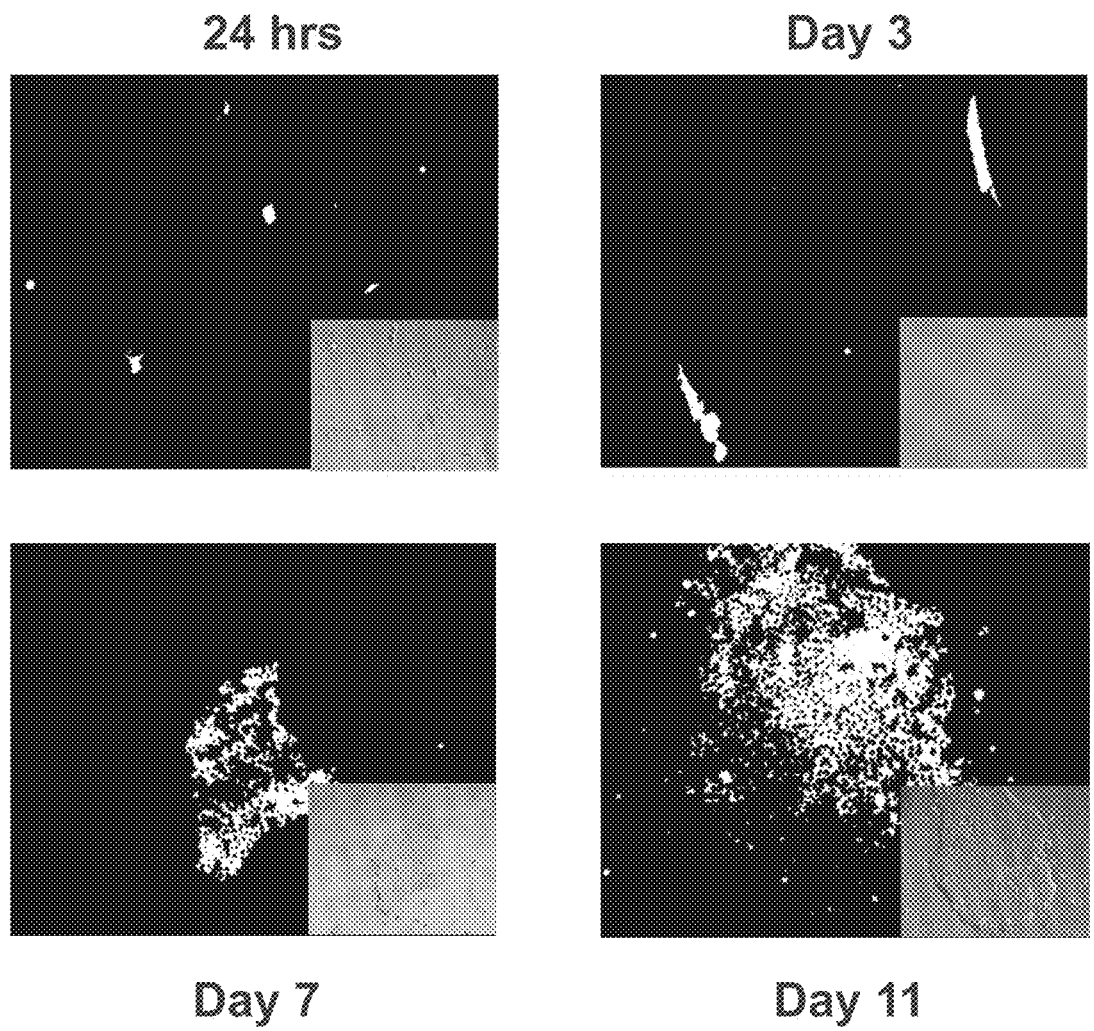
FIG. 3 shows fluorescence micrographs of human ES cell colonies at various times after stable transfection with a transposon expression vector driving expression of eHLA-G and EGFP.
Figure 4:
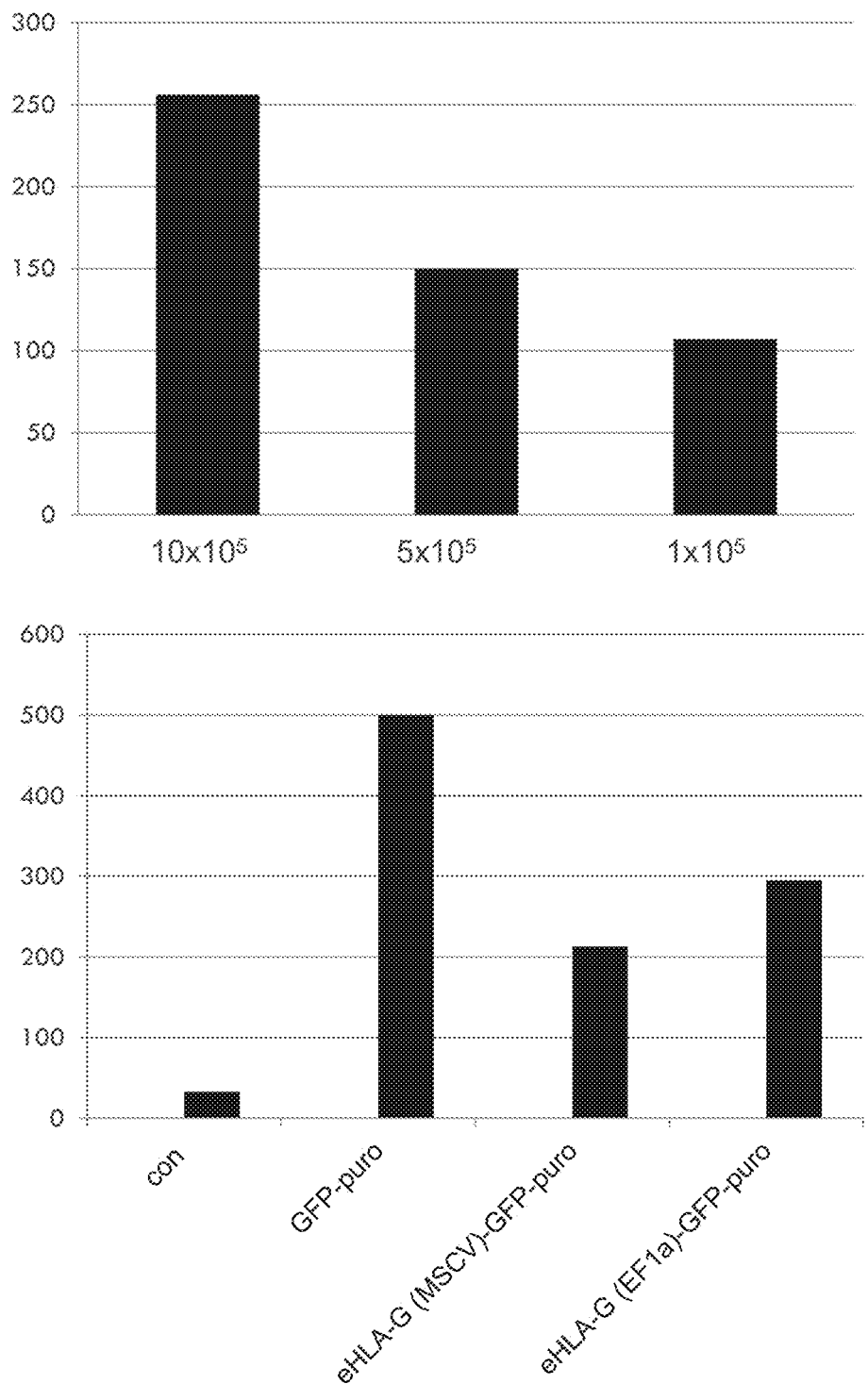
FIG. 4 (Top Panel) shows a bar graph depicting the relationship between the starting number of hES cells transfected with an EGFP-containing expression vector and the fraction of EGFP$^+$ cells detected in the cell population at 10 days post-transfection. The numbers on the x-axis are the number of GFP$^+$ colonies per $5\times10^5$ cells. The numbers on the y-axis are the cell number. (Bottom Panel) shows a bar graph depicting the relationship between various transposon vectors (using different promoters) and the fraction of EGFP$^+$ cells detected in the cell population. The numbers on the x-axis are the number of GFP$^+$ colonies per $5\times10^5$ cells. For the bottom panel, from left to right: control (con), GFP-puro (size of transfected vector is 7.3 kb); eHLA-G (MSCV)-GFP-puro (size of transfected vector is 8.6 kb); and eHLA-G (EF-1α)-GFP-puro (size of transfected vector is 9.2 kb). Additional eHLA-G (EF-1α)-GFP-puro transfection efficiency experiments (not shown) were conducted, which indicated that at 10 days post-transfection, the highest efficiencies (~500 GFP$^+$ colonies per $5\times10^5$ cells) were obtained in solution V and program B16 after selection with puromycin for 10 days.
Figure 6:
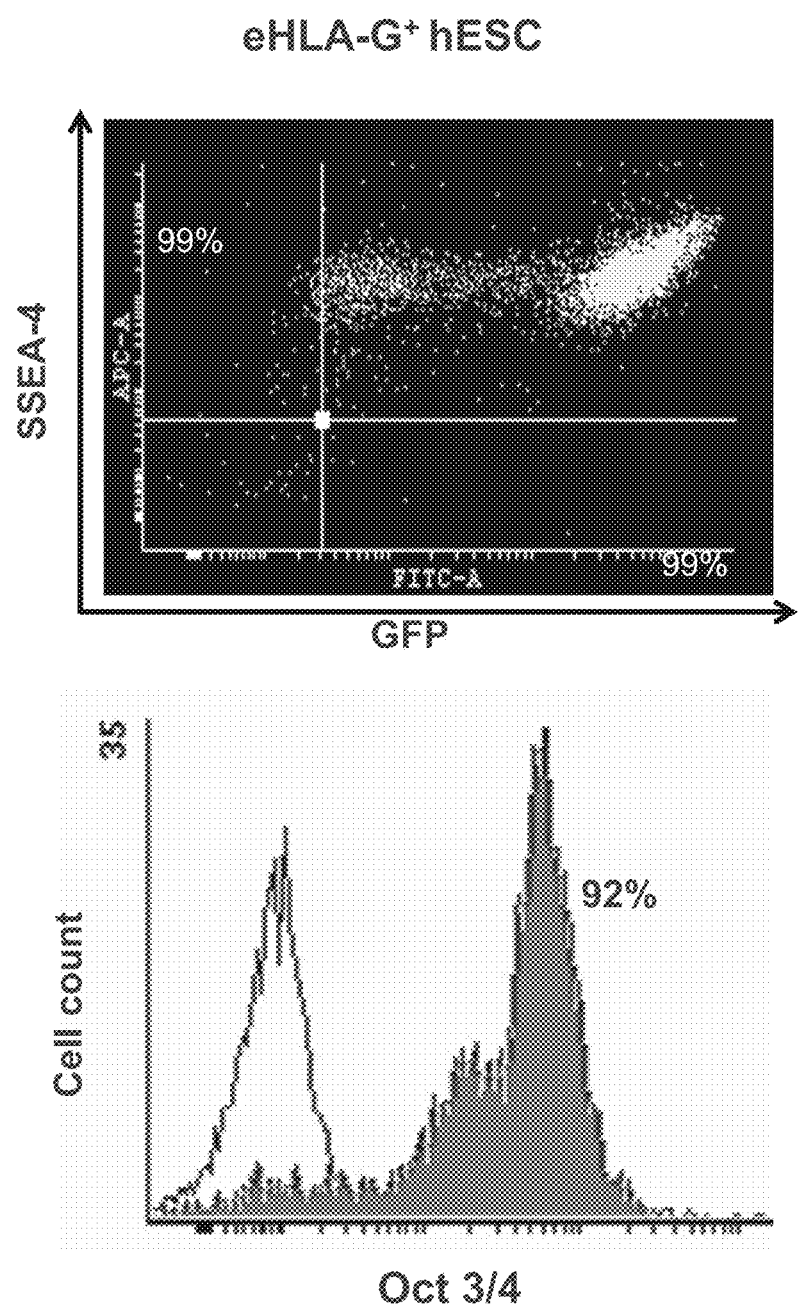
FIG. 6 (Top Panel) shows a flow cytometry scattergram showing the distribution of SSEA-4$^+$/GFP$^+$ double-positive cells in a population of eHLA-G-modified hES cells. (Lower Panel) shows the distribution of Oct 3/4$^+$ cells in the population of eHLA-G-modified hES cells. SSEA-4 and Oct 3/4 are pluripotency markers. This data, along with FIG. 5, indicate that eHLA-G-modified hES cells maintained their characteristic self-renewal pluripotency markers. Additionally, eHLA-G(EF-1α)-GFP-hESCs maintained their pluripotency and normal karyotype in vivo. Humanized NSG mice were injected subcutaneously with eHLA-G(EF-1α)-GFP-hESCs, and teratoma formation was observed, indicating that the injected/transplanted cells were not rejected as hESCs exhibited reduced immunogenicity and/or increased immunosuppression. The karyotype of the teratoma cells were normal.
Figure 7:
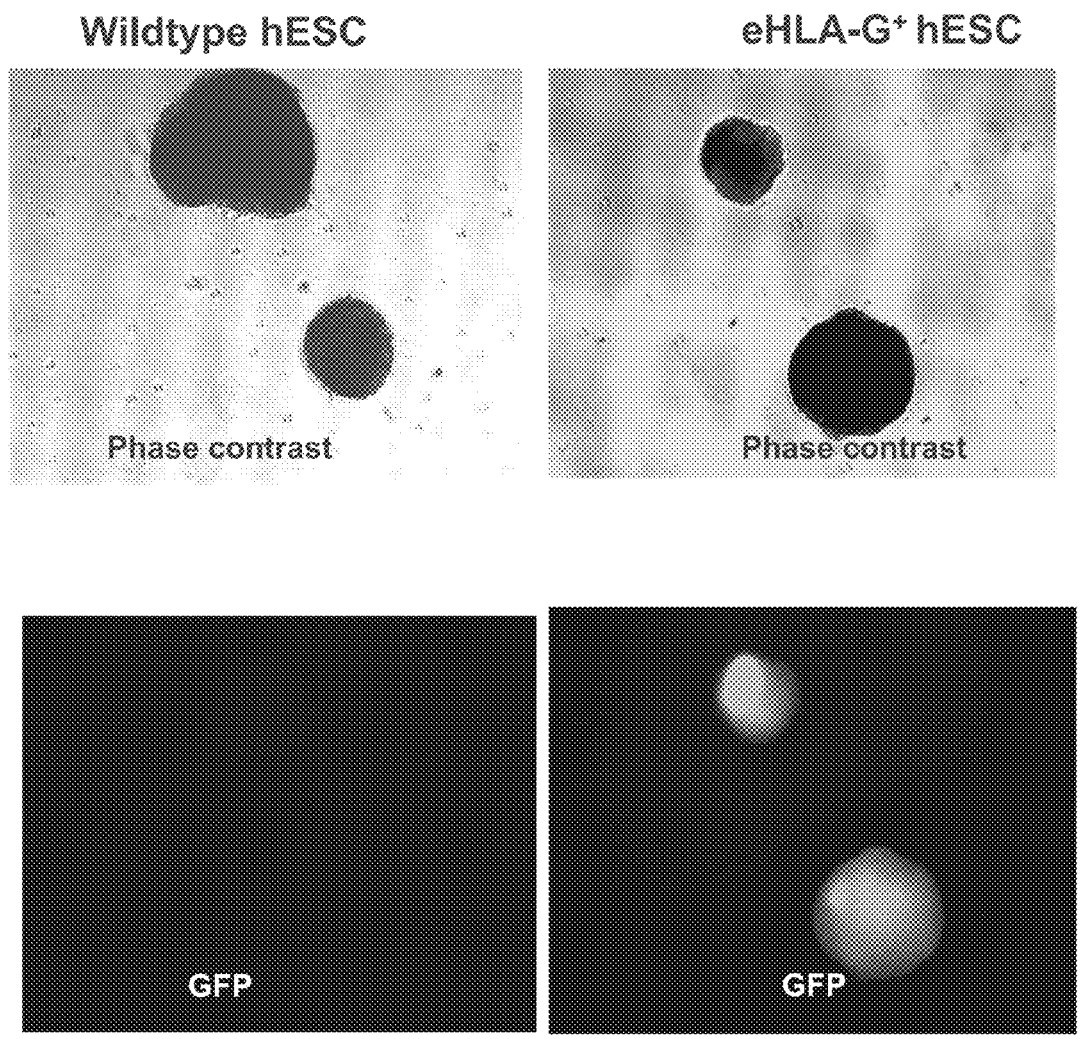
FIG. 7 (Top Panel) shows phase contrast photomicrographs of Wildtype (left picture) and eHLA-G modified hESC-generated (right picture) embryoid bodies (EBs) at day 15. (Bottom Panel) shows a fluorescence micrograph of the EBs shown in the Top Panel. No GFP signal is detected in the wildtype hESC EB, whereas strong GFP expression is detected in both of the eHLA-G modified hESC EBs. This data indicates that eHLA-G$^+$ hESCs maintain EB formation.
Figure 8:
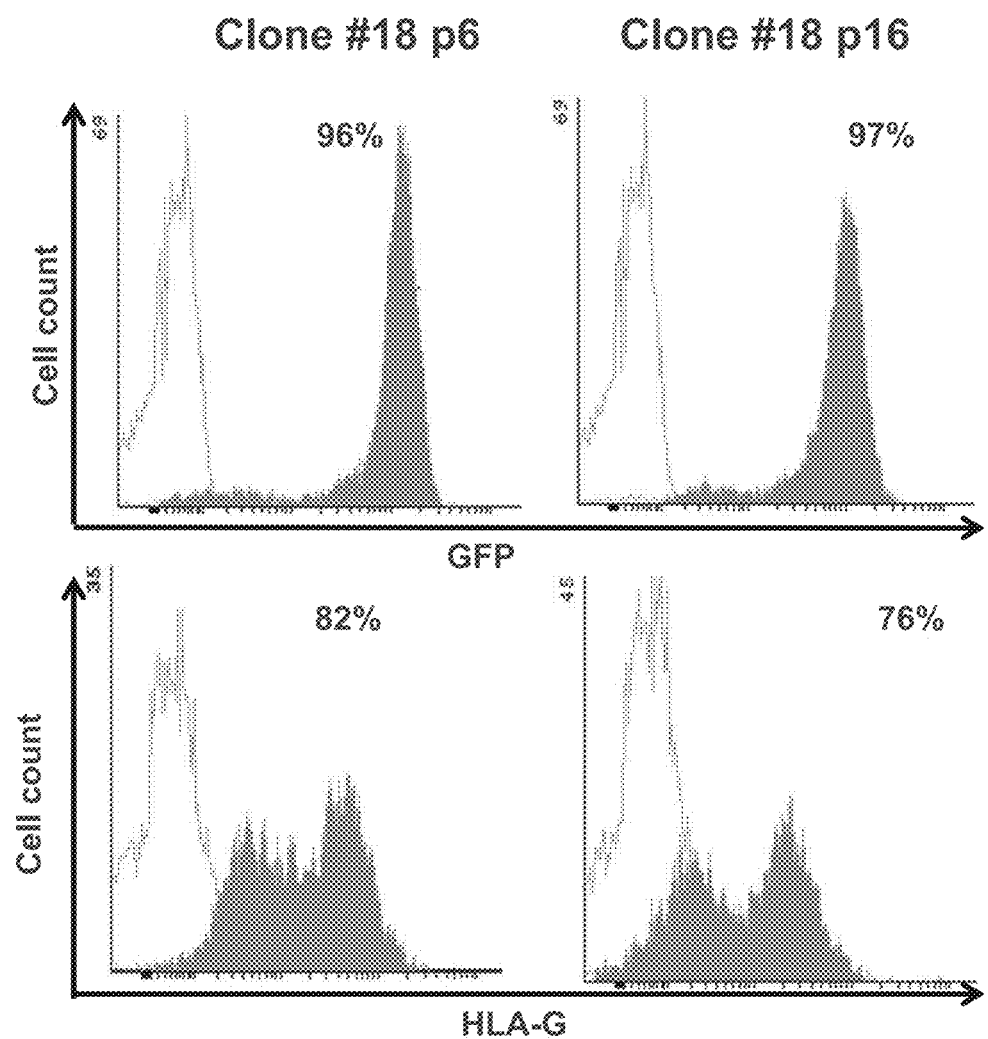
FIG. 8 shows that eHLA-G$^+$ hESCs are silencing resistant. (Top Panel) shows a flow cytometry distribution histogram for the expression of GFP in a eHLA-G modified hESC-line, which demonstrated similar strong expression of GFP after 6 and 16 passages. (Bottom Panel) shows a flow cytometry distribution histogram for the expression of HLA-G in the same hESC line, again showing persistent expression of the eHLA-G transgene at both passage 6 and 16.
Figure 9A:
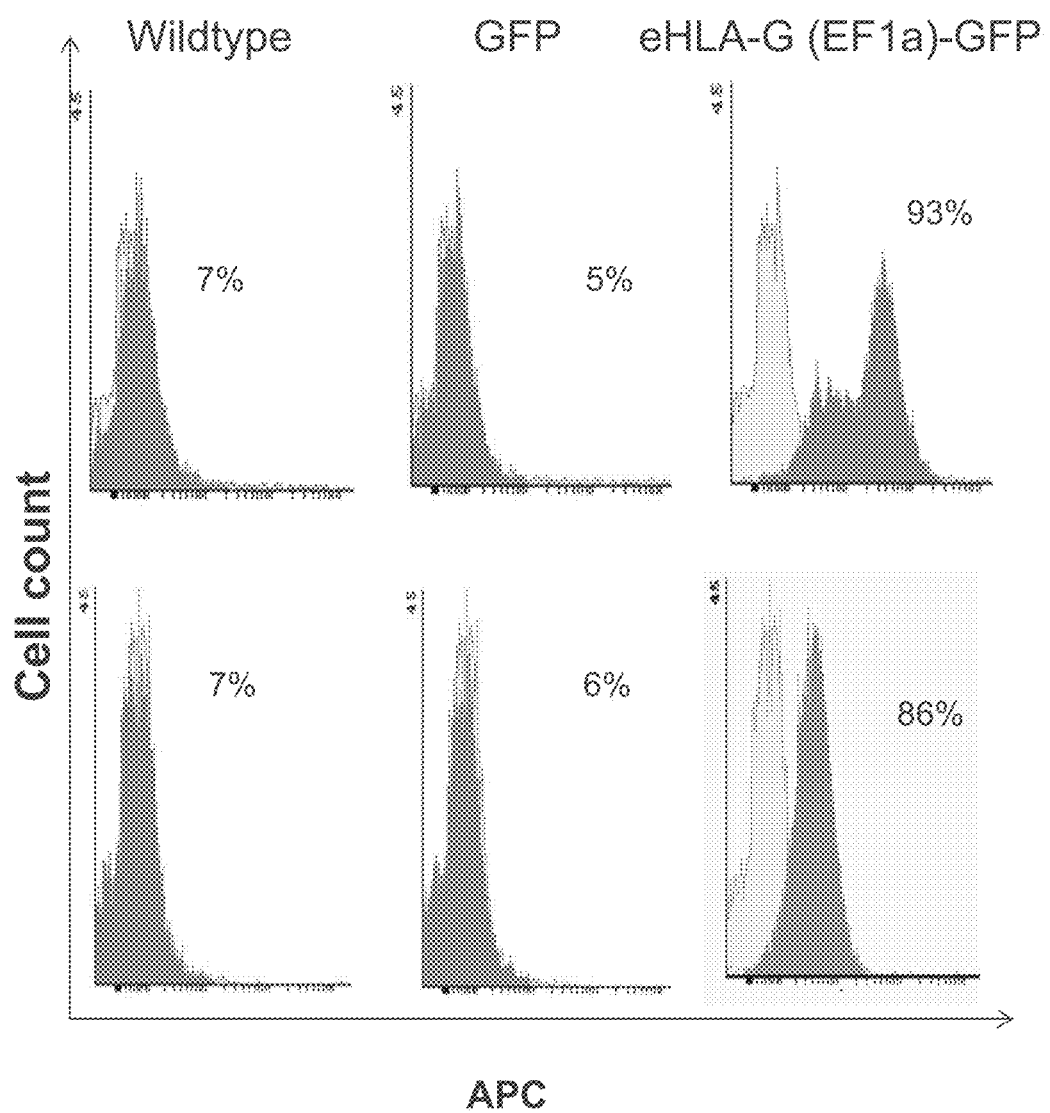
FIG. 9A (Top Panel) shows flow cytometry distribution histograms for total (intracellular) expression HLA-G in wildtype (left histogram), GFP-modified (middle histogram), and eHLA-G(EF-1α)-GFP modified hESCs (right histogram). (Bottom Panel) shows flow cytometry distribution histograms for surface expression HLA-G in wildtype (left histogram), GFP-modified (middle histogram), and eHLA-G (EF-1α)-GFP modified hESCs (right histogram).
Figure 9B:
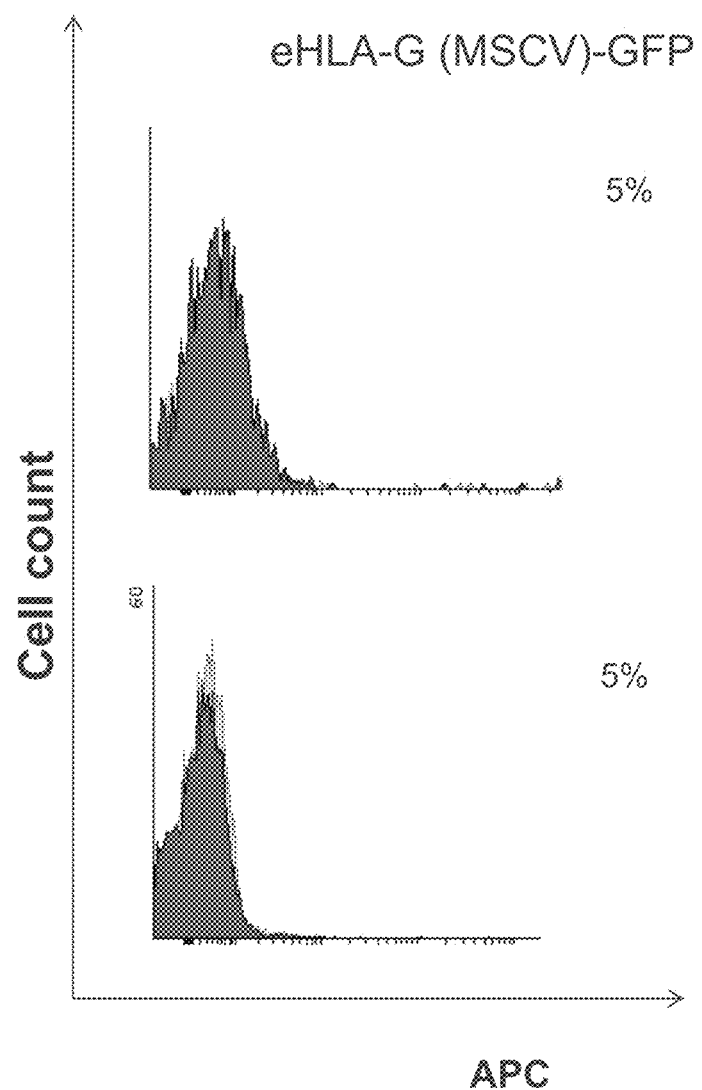
FIG. 9B (Top Panel) shows a flow cytometry distribution histogram for total expression HLA-G in eHLA-G(MSCV)-GFP modified hESCs.

Example 4 Assessment of the ePiggyBac Gene Delivery System eHLA-G transfection efficiency was determined by plating the transfected cells in CM plus Y-27632 at $2 \times 10^3$ cells per 6 cm dish for 24 hours, and then changing to CM alone. Medium was then changed daily for seven days, and colonies were evaluated by live cell staining and immunofluorescence microscopy, as discussed in Example 5. For each clone, three high power fields were counted and the percentage of reporter protein⁺/eHLA-G⁺ hESCs was calculated. Results of this experiment are shown in FIGS. 3-4. The eHLA-G insertion site was determined using a plasmid rescue strategy as described in Lacoste et al supra. Briefly, genomic DNA was isolated from transgenic hESC clones and digested with BamHI/BglIII/NotI, self-ligated at low concentration with T4 DNA ligase overnight at 16° C., precipitated with 100% isopropanol, and washed with 70% ethanol before transformation in DH10B E. coli and selected on ampicillin. eHLA-G copy number was determined using SplinkTA PCR. Standard G-banding was performed every 20 passages to assess karyotype stability. eHLA-G and reporter protein gene silencing were assessed every 10 passages using flow cytometry. Prior to dissociation and analysis, hESCs were treated for one hour with 10 µM Y-27632. Cells were then dissociated with 0.25% trypsin-EDTA at 37° C. for five minutes, washed in CM plus Y-27632, resuspended in ice-cold PBS containing 0.1% BSA and 0.5 mM EDTA, and then analyzed using a BD FACS Canto II flow cytometer (Becton Dickinson). As shown in FIGS. 8 and 9, at passage 16, essentially no silencing of EGFP or eHLA-G expression was observed. Pluripotency was assessed every 20 passages by immunocytochemical detection of the following: 1) pluripotency markers Oct3/4, SSEA-4, Sox2 and Nanog (FIGS. 5 and 6), 2) reporter protein$^+$/eHLA-G$^+$ embryoid body formation (FIG. 7), and 3) the endodermal marker Gata 6, mesodermal marker muscle actin, and ectodermal marker neurofilament heavy chain in differentiated transgenic hESCs (data not shown), all using a Leica CTR6500 fluorescent microscope. All antibodies were from Abcam unless otherwise specified.

Example 5 Cell Surface Localization of eHLA-G and Other HLA Proteins

Figure 5:
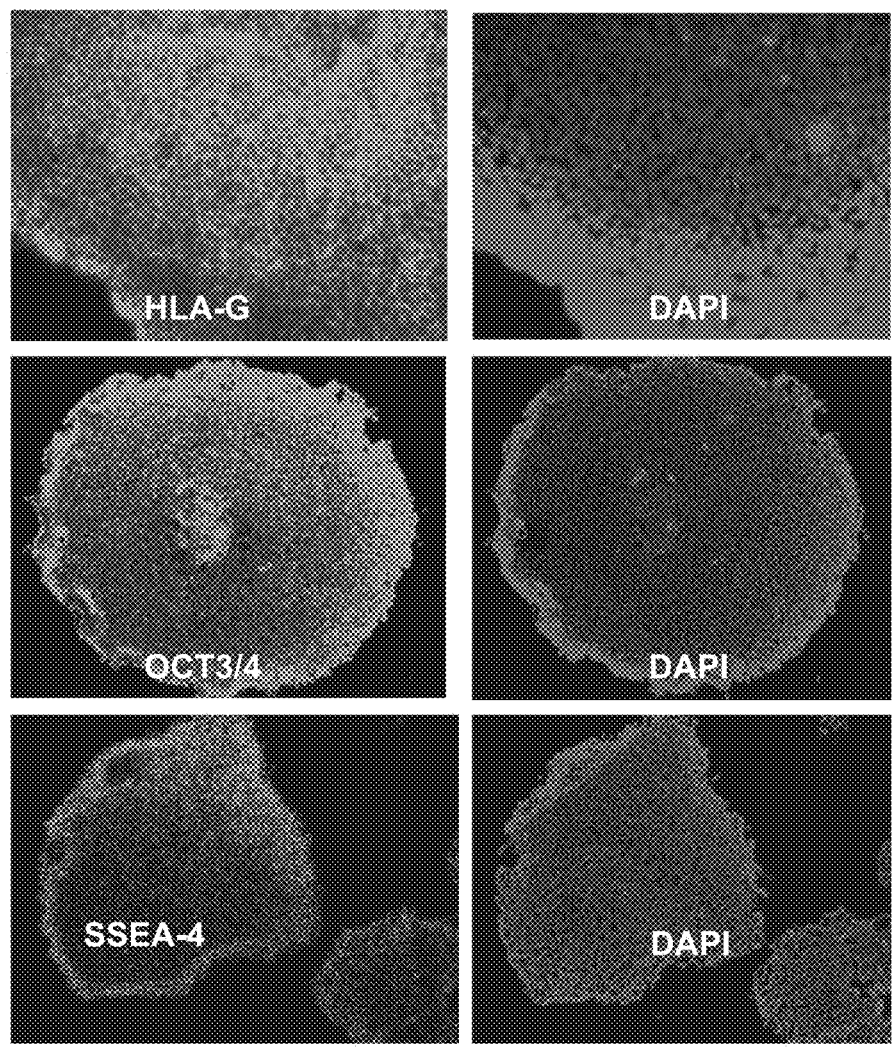
FIG. 5 shows a series of immunofluorescence micrographs showing expression in HLA-G modified human ES cells of HLA-G expression and DAPI staining (top images); Oct 3/4 and DAPI (middle images); and SSEA-4 and DAPI (bottom images).

Live cell staining was used to detect cell surface HLA class Ia, HLA-E, eHLA-G, and HLA class II expression in transgenic versus wildtype hESCs and hEEPs. Briefly, cells were harvested and washed in cold PBS, stained with the corresponding 1 mAb in PBS containing 10% goat serum and 3% BSA for 60 min at 4° C., washed, fixed with 1% paraformaldehyde for 10 min, and subsequently stained with a goat anti-mouse IgG conjugated with FITC for 30 minutes at 4° C. Control aliquots were stained with an isotype-matched IgG to evaluate nonspecific binding to target cells. Each antibody (MEMG/9 for HLA-G, MEM-E/08 for HLA-E, Bub for HLA class Ia, and HKB1 (Abbiotec, San Diego, Calif.) for HLA class II) was first tested at several dilutions in order to determine the optimal conditions for achieving specific-only binding. After staining, cells were smeared on a glass slide, allowed to air dry, and then mounted with anti-fade media containing DAPI (Vector Laboratories). Slides were observed immediately under a Leica CTR6500 fluorescence microscope. As shown in FIGS. 5 and 10, expression of HLA-A,B,C; HLA-E, HLA-DP, DQ, DR, and β-microglobulin were similar in wildtype and eHLA-G modified human ES cells, whereas an approximately seven-fold higher level of HLA-G expression was observed in the eHLA-G modified human ES cells.

Example 6 Assessment of eHLA-G Expression on NK-92 Cell-Induced Cytotoxicity eHLA-G-expressing hESCs were cultured and differentiated into hEEPs as described in Example 2. NK-92 cells (CRL-2407, American Type Culture Collection, Manassas, Va.) were cultured in Minimum Essential Medium Alpha Medium (α-MEM, Invitrogen) supplemented with 12.5% FBS, 12.5% horse serum, 0.2 mM inositol, 0.1 mM β-mercaptoethanol, 0.02 mM folic acid and 100 IU/ml recombinant IL-2 (Sigma) at 37° C. in a 5% $CO_2$ humidified incubator.

Cytotoxicity was performed using a CytoTox96 Non-Radioactive Cytotoxicity Assay Kit (Promega, Madison, Wis.) as the protocol instructed. Briefly, effector cells were mixed with $5\times10^3$ target cells at various NK-92 (Effector or "E") to hESCs or hEEPs (target or "T") E:T cell ratios in U-bottom 96 well plates (Costar, Cambridge, Mass.). After 4 h at 37° C. in a humidified 5% $CO_2$ incubator, 50 μl of the supernatant was collected to determine the LDH release. Target cell spontaneous release and maximal release of LDH and the effector cell spontaneous release of LDH were determined by incubating these cells in medium alone. Each assay was performed in triplicate and the results were expressed as percentages of lysis %. The percentage of specific lysis was determined as follows: (experimental release−effector spontaneous release−target spontaneous release/target maximum release−target spontaneous release)×100. In all experiments spontaneous release was <10% of maximum release.

Figure 11:
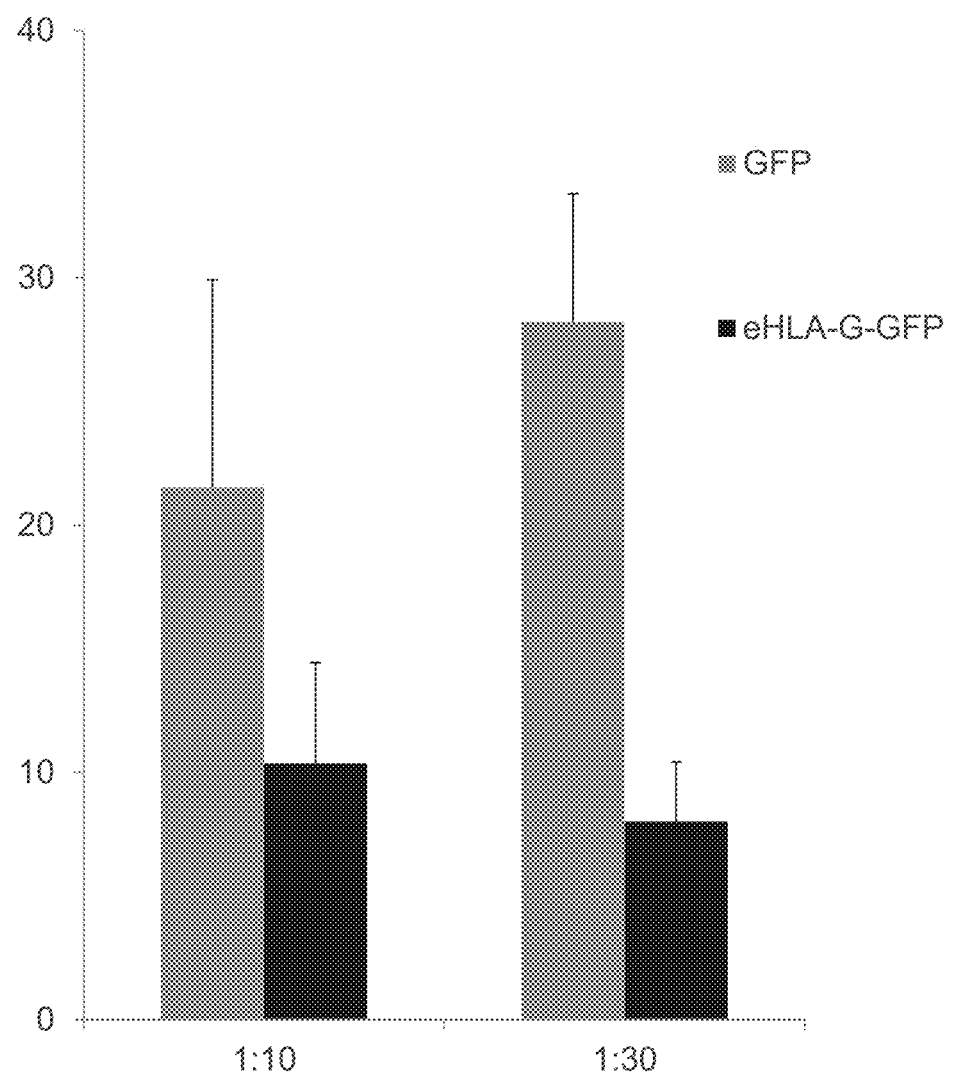
FIG. 11 shows that NK92 cytotoxicity effect is greatly suppressed by eHLA-G$^+$ hESCs. (See Example 6 for further description.) The figure shows a bar graph illustrating the results of an NK92 cell cytotoxicity assay. The 1:10 and 1:30 values indicate the ratio of effector (NK92) to target cells (GFP transgene alone control wild-type cells or eHLA-G-GFP transgene modified cells). This is an in vitro assay to determine the immunogenicity of eHLA-G modified hESCs (black bars; eHLA-G-GFP) compared to wildtype hESCs (grey bars; GFP). eHLA-G modified hESCs exhibit substantially reduced cytotoxicity in the presence of NK92 cells as compared to the case for wildtype hESCs. This data indicates that exogenous HLA-G expression can provide improved donor capabilities for such genetically modified cells, as reduced cytotoxicity in the presence of NK92 cells shows that such genetically modified cells have reduced immunogenicity and/or improved immunosuppression. Results are the average of four experiments. See Example 6 for further description.
Figure 14:
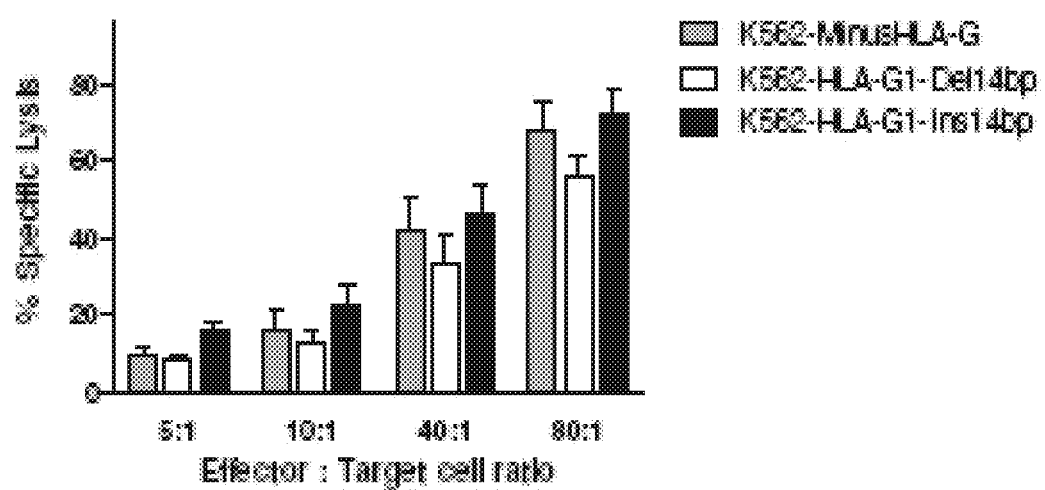
FIG. 14 (Effect of K562-HLA-G1 14 base pair (bp) insertion/deletion polymorphism on cytotoxic activity of NK cells.) The figure shows a bar graph comparing NK cell-mediated cytotoxicity (% specific lysis) on wildtype K562 cells (grey bars), K562 cells expressing an HLA-G variant with a 14 bp insertion in the 3' UTR (Ins14bp) (black bars), and K562 cells expressing an HLA-G variant with a 14 bp deletion in the 3' UTR (Del 14bp) (grey bars). There are four sets of data with different effector (NK cell) to target cell (K562 cells) ratios.
Figure 15:
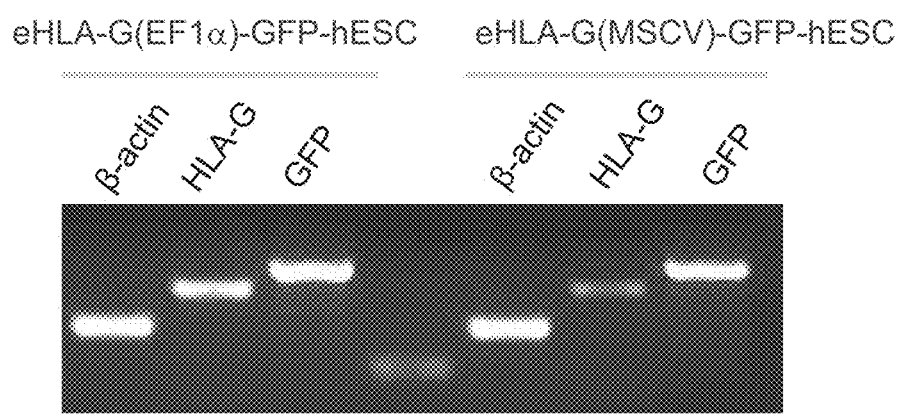
FIG. 15 provides data that indicates that HLA-G transgene expression is significantly influenced by promoter activity. RT-PCR shows that both GFP and HLA-G transcripts were highly expressed in eHLA-G (EF-1α)-GFP-hESC cell lines. Immunofluorescence also shows that both GFP and HLA-G proteins were highly expressed in HLA-G (EF-1α)-GFP-hESC cell lines (not shown here). However, HLA-G transcripts or proteins were rarely detected in HLA-G (pMSCV)-GFP-hESC lines, whether by RT-PCR or immunofluorescence, even though GFP expression was high in these cells. (Data not shown here.) Thus, EF-1α promoters are preferred in certain embodiments of HLA-G transgene expression.

As shown in FIG. 11, at an E:T ratio of 1:10, killing of eHLA-G expressing hESCs was reduced by over 50% relative to wildtype cells expressing GFP alone. At an E:T of 1:30, killing of eHLA-G expressing hESCs was reduced by approximately 75%. Wildtype hESCs were killed at a reasonable rate as shown for both E:T ratios (GFP alone). Further, it was shown that expression of the 3' UTR (Del 14 bp) HLA-G allele in K562 cells results in diminished NK cell-induced cytotoxicity relative to that observed in K562 cells expressing the (Ins 14 bp) HLA-G allele, as well as in unmodified K562 cells. See FIG. 14.

Figure 18:
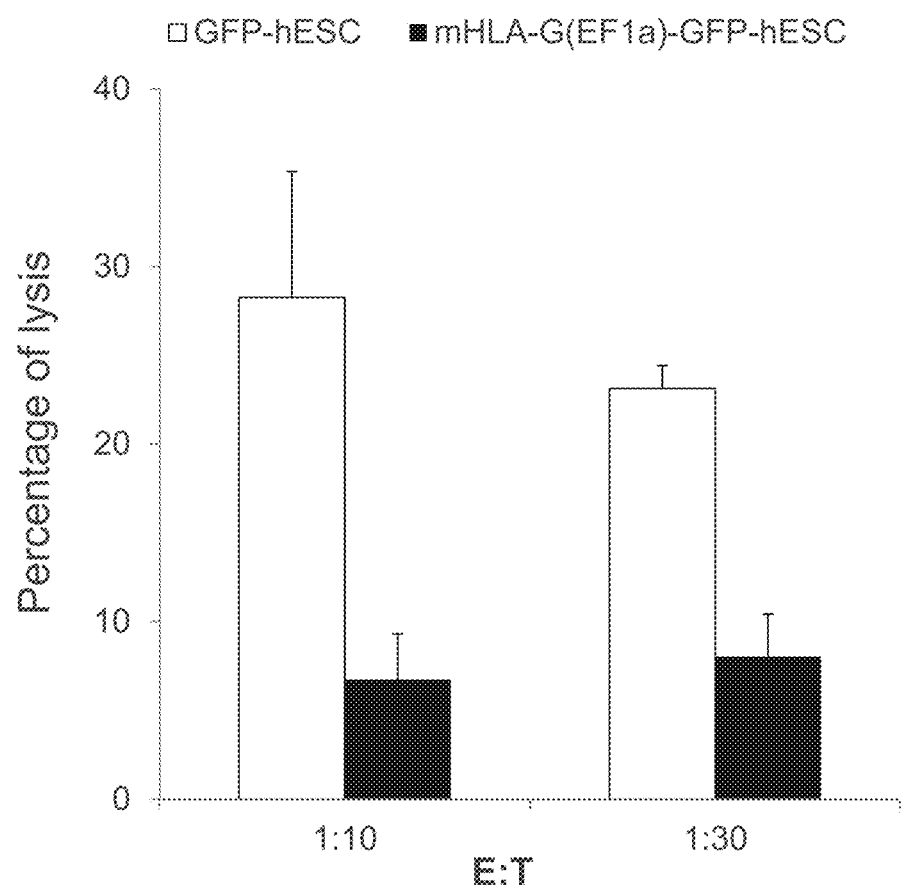
FIG. 18. The results of FIG. 11 were repeated and confirmed in additional NK cytotoxicity experiments. As shown, killing of eHLA-G(EF-1α)-GFP-hESCs was reduced more than 100% as compared to controls hESCs that contained only a GFP transgene (no HLA-G transgene).

The results of FIG. 11 were repeated and confirmed in additional NK cytotoxicity experiments. As shown in FIG. 18, killing of eHLA-G(EF-1α)-GFP-hESCs was reduced more than 100% as compared to controls hESCs that contained only a GFP transgene (no HLA-G transgene). This data shows that HLA-G transgene expression imparts immunosuppressive and/or reduced immunogenicity characteristics in hESCs.

NK cytotoxicity experiments were also conducted on hEEPs differentiated from hESCs. As shown in FIG. 19, killing of eHLA(EF-1α)-GFP-hEEPs differentiated from eHLA(EF-1α)-GFP-hESCs was reduced well more than 100% (about 3-fold) as compared to control hEEPs. This data shows that eHLA(EF-1α)-GFP transgene is stable and persistent throughout the process of differentiation, and that HLA-G expression is able to impart immunosuppressive and/or reduced immunogenicity characteristics in differentiated cells.

Example 7 Determination of the Immunogenicity of e-HLA-G$^+$ Cells In Vivo by Allografts in Humanized Mice A humanized mouse model with human peripheral blood lymphocytes (Hu-PBL-NSG), but not wildtype immunodeficient NSG mice, was recently shown to reject mismatched human islets within 1-2 weeks post-transplantation (King et al (2008), *Clin Immunol*, 126:303-314). Although graft-versus-host-disease (GVHD) sets in at 4-5 weeks, graft survival is monitored until euthanasia criteria are met. The presence of only lower levels of GVHD allows us to extend our observation window. NSG mice (females at six weeks of age) were purchased from Jackson Laboratory and handled in accordance with the guidelines of the Institutional Animal Care and Use Committee and the recommendations in the Guide for the Care and Use of Laboratory Animals (Institute of Laboratory Animal Resources, National Research Council, National Academy of Sciences). Functional humanized NSG mice were generated by intravenous injection of about $20\times10^6$ human PBMCs into NSG mice according to (Pearson et al (2008), *Curr Protoc Immunol*, Ch. 15:Unit15.21; and King et al supra). Engraftment was verified at about four weeks by collecting blood from the retroorbital venous plexus of anesthetized mice using EDTA-coated capillary tubes (Drummond Scientific) and EDTA-treated 1.5 ml tubes (Eppendorf). Cells were then processed for human CD45 positivity by FACS analysis according to King et al supra. Levels of human CD45$^-$ cells reaching 0.1% in the blood at four weeks is considered a successful engraftment and allows allorejection studies.

The hESC and hEEP culture systems that are typically used, expose cells to immunogenic animal derivatives such as the sialic acid Neu5Gc (Martin et al (2005), *Nat Med*, 11:228-232). Thus, a decontamination step can be added that was recently shown to significantly reduce Neu5Gc levels (Heiskanen et al (2007), *Stem Cells*, 25:197-202). hESCs can be decontaminated of Neu5Gc using two approaches: 1) culturing in TeSR1 media supplemented with bFGF, LiCl, GABA, and pipecolic acid on human matrix coated plates according to the method of Ludwig et al (2006), *Nat Biotechnol*, 24:185-187, and 2) KSR replacement by heat-inactivated blood group AB Rh⁻ human serum (Heiskanen et al (2007), *Stem Cells*, 25:197-202. hESCs cultured under both methods can be assessed by incubation with anti-Neu5Gc mAb and analyzed by flow cytometry. The second approach may be adopted, as the method of Ludwig et al may require hESC adaptation. hEEPs are cultured in DFSM that lacks animal derivatives per its manufacturer.

The objective of performing allografts with HLA-G modified cells is to assess whether HLA-G expression reduces immunogenicity as indicated by an increase in tumor size. Prior to transplantation, the intended injection site was shaved to facilitate clinical observation. Animal guidelines including appropriate use of anesthesia were followed at all times. $5 \times 10^6$ transgenic eHLA-G⁺ and HLA-G⁻ hESCs were resuspended in 100 μl of the appropriate media containing India ink to mark the injection site. This facilitates histological assessment should insufficient fluorescence be observed. Cells were injected subcutaneously into the thoracic mammary fat pad of five 3-month old Hu-PBL-NSG mice. The results of these allografts are shown in FIGS. 20 and 21. The "G0" hESCs are the control ESCs that do not contain an eHLA-G transgene, but rather only GFP. "mG1 (#1)" and "mG1(#2)" refer to two different eHLA-G(EF-1α)-GFP nucleofected hESC clones. The G0, mG1(#1), and mG1(#2) tumors, as shown in FIG. 20, were measured and weighed. The G0 hESCs formed a tumor with a volume of 126.9 cubic millimeters and a weight of 32 milligrams. The mG1(#1) hESCs formed a tumor with a volume of 748.4 cubic millimeters and a weight of 318 milligrams. The mG1(#2) hESCs formed a tumor with a volume of 1116.7 cubic millimeters and a weight of 675 milligrams.

FIG. 21 shows the averaged results of tumors from hESC allografts onto five humanized NSG mice. The data shows that HLA-G nucleofected hESCs ("mG1") formed much larger (more than 3-fold by volume) and heavier (more than 2-fold by weight) tumors than wild-type hESCs ("G0") transplanted into humanized NSG mice. Thus, the data indicates that eHLA-G transgene expression can provide reduced immunogenicity and/or increased immunosuppression. This supports the general application of the eHLA-G transgene constructs described herein for modifying any desired cell-type into a universal or superior allogenic donor for therapy, transplants, tissue repair, cell and tissue substitutes, and the like.

The above-described allograft experiments with humanized NSG mice can be conducted with any eHLA-G modified cell-type that actively proliferates or can be induced to proliferate.

In addition, allografts in humanized mice can be monitored using a Spectrum In Vivo Imaging System (Caliper, Mountain View, Calif.) with a 620 nm emission filter and 2.5 second exposure time. At wavelengths of 620 nm or greater, the autofluorescence experienced with GFP is eliminated and signal can be detected as deep as 2.5 cm beneath the surface of the skin (Shaner et al (2004), *Nat Biotechnol*, 22:1567-1572). Mice are longitudinally imaged and weighed on a weekly basis. If no signal is observed during the four week period, mice are sacrificed and the injected thoracic mammary fat pad is assessed histologically using fluorescence microscopy to detect the fluorescent reporter protein used. In all cases, upon sacrifice of mice, tissue is stained with hematoxylin and eosin to assess for teratoma formation and immune rejection. Immunohistochemistry is also be performed to detect human β2 microglobulin (PBMCs, hESCs, hEEPs) and CD45 (PBMCs), with the latter serving as a supplemental measure of immune cell infiltration of the allograft. Slides are read by an expert pathologist blinded to the experimental conditions.

Example 8 Assessment of the Tumorigenicity of eHLA-G+- and HLA-G⁻-hEEPs

The impact of eHLA-G on hEEP tumorigenicity is assessed by injecting transgenic G⁺ and non-transgenic G⁻-hEEPs using a similar protocol as discussed in Example 8 except that cells are transplanted into non-humanized NSG mice. A total of 14 mice are monitored using longitudinal fluorescent live animal imaging and weight assessment on a monthly basis for up to the earlier of nine months or meeting euthanasia criteria. Mice are then sacrificed and the injected thoracic mammary gland harvested in 4% neutral-buffered paraformaldehyde. Fixed tissue is transferred to 70% ethanol and embedded in paraffin. Sections are stained with hematoxylin and eosin and processed for fluorescent reporter protein microscopy. If the tissue sections are found to be reporter protein-negative, they are stained using mAbs specific to human β2 microglobulin and CD45, with the latter serving to ensure the presence of non-PBMCs at the injection site.

The statistical significance of independent means is assumed for p values of <0.05. Two-sample mean comparisons are determined using a Student's t test. Comparisons of three or more means are made using one- or two-way analyses of variance, and Bonferroni's post-hoc test. All measures of variance are presented as standard error of the mean. A linear regression is performed to compare the relationship between in vitro and in vivo data to determine if the former has predictive value towards human allograft rejection in the Hu-PBL-NSG mouse model that is used in this study. For example, the percentage increase in alloproliferation in vitro will be regressed against the PBMC-matched pair used in the in vivo phase (output is the level of reporter protein fluorescence at four weeks post-transplantation). A successful outcome here is a high $R^2$ value and negative slope coefficient, suggesting that eHLA-G expression leads to increased engraftment. Such an interpretation is contingent on a high correlation between eHLA-G expression and reporter protein positivity in the clones selected for use in the in vitro and in vivo studies.

Example 9 Immunosuppression and Immunogenicity Assessment of eHLA-G Stably Transfected into Fully Differentiated Fibroblasts The eHLA-G(EF-1α)-GFP transgene and control constructs were transfected into human newborn dermal fibroblasts (a cell-type that is already fully differentiated) using nucleofection. Human newborn dermal fibroblast cells (HFD) were purchased from ATCC and cultured in Iscove's Modified Dulbecco's Medium (IMDM) (ATCC) supplemented with 10% FBS and 1% PS (Invitrogen). When the cells reached 80% confluence, cells were harvested by incubating with 0.25% Trypsin-EDTA (Invitrogen) for 3 minute at 37° C. Cells were counted and $0.5 \times 10^6$ were centrifuged and resuspended in human dermal fibroblast nucleofection solution (Cat. No. VPD-1001, Lonza, Walkersville, Md.). Helper and transposon plasmids were added to the cell suspension, and nucleofection was performed with program setting U-020 according to the manufacturer's protocol (Lonza). Cells were then plated in 6-well plates and incubated in humidified 37° C./5% $CO_2$ for 24 h. After 24 h, the stable transfected cells were selected with 1 μg/ml puromycin (Sigma) for 7 days. Stable GFP-positive cells were maintained in 500 ng/ml puromycin and HLA-G and GFP expression were detected with flow cytometry. Stable transfectants were maintained in culture for use in peripheral blood mononuclear cell (PBMC) proliferation assays and NK-92 cytotoxicity assays as described below.

PBMC proliferation assays. Human dermal fibroblasts stably transfected with the eHLA-G(EF-1α)-GFP transgene ("HFD-m1-GFP" cells) or GFP-alone control construct ("HFD-G0-GFP" cells) were assessed for their ability to inhibit PBMC proliferation. HFD-G0-GFP and -mG1-GFP cells were inactivated with Mitomycin C (10 μg/ml for 2.5 h) and seeded at $3.0 \times 10^3$/well in 96-well plate and allowed to adhere for 24 h. $1 \times 10^5$ PBMC in the presence of 6 μg/ml PHA were added in triplicates in the corresponding HFD cells. HFD-G0-GFP and -mG1-GFP cells alone were included for MTT-OD correction. ("MTT" is a pale yellow substrate reagent that is cleaved by living cells to yield a dark blue formazan product. This process requires active mitochondria, and even freshly dead cells do not cleave significant amounts of MTT. MTT therefore provides a colorimetric assay that can be used for either proliferation or cytotoxicity assays.) PBMC without PHA and PBMC with 6 μg/ml of PHA were included as controls. Co-cultures were incubated for 3 days and PBMC-proliferation was estimated using MTT reagent using the following formula: % PBMC proliferation=[(OD570 of HFD/PBMC/PHA−OD570 of HFD)/(OD570 of PBMC/PHA)]×10. As shown in FIG. 22, the HFD-mG1-GFP clone "mG1-R1" suppressed PBMC proliferation greater than controls and other clones, indicating that exogenous HLA-G expression can provide immunosuppression and/or reduced immunogenicity for differentiated cells, such as fibroblasts.

NK-92 cytotoxicity Assays. The assays were performed substantially as described previously. Briefly, $2.5 \times 10^3$ target cells (i.e., HFD-m1-GFP cells or HFD-G0-GFP cells) were incubated with NK-92 cells at 3:1, 10:1, 30:1 E:T ratio in CTL media for 7 hr. K562-WT cells were included as positive control for NK-92 cytotoxicity. Cytotoxicity was determined with a CytoTox96 cytotoxicity assay kit The percentage of specific lysis was determined as follows: % specific lysis=[(experimental LDH release−effector spontaneous release−target spontaneous release)/(target maximum release−target spontaneous release)]×100. As shown in Table 4 below, the HFD-mG1-GFP clones "mG1-R1" and "mG1-#1" suppressed NK-92 cytotoxicity greater than controls and other clones, indicating that exogenous HLA-G expression can provide immunosuppression and/or decreased immunogenicity for differentiated cells, such as fibroblasts.

TABLE 4

Cytotoxicity of NK-92 Against HFD-G0 and HFD-G1 Target Cells

| Target cell | % cytotoxicity | | |
|---|---|---|---|
| ($2.5 \times 10^3$) | 10:1 | 30:1 | 60:1 (E:T) |
| HFD-G0-2 | 0 | 0 | 1.5 |
| HFD-mG1-#1 | 0 | 1 | 4 |
| HFD-mG1#3 | 0 | 0 | 0 |
| HFD-mG1-R1 | 0 | 1 | 4 |
| HFD-mG1-R2 | 2 | 1 | 9 |
| K562-WT | X | 36 | 44 |

The invention claimed is:

1. A method of producing a genetically modified mammalian cell that has reduced immunogenicity and/or improved immunosuppression as compared to a mammalian cell without said genetic modification, the method comprising: stably transfecting an isolated mammalian cell with an exogenous nucleic acid comprising:
   a. a nucleic acid sequence encoding a Human leukocyte antigen-G (HLA-G) protein comprising a full length amino acid sequence of SEQ ID NO:2, and operably linked to an Elongation Factor-I alpha (EF-1α) promoter comprising a sequence of SEQ ID NO:6; and
   b. a 3' untranslated region (UTR) comprising a full length nucleotide sequence of SEQ ID NO:3;
   wherein the encoded HLA-G protein is expressed by the genetically modified mammalian cell for at least seven weeks, and wherein the reduced immunogenicity and/or improved immunosuppression of the genetically modified cell is determined by either:
   (1) a reduction of natural killer cell, NK-92 cytotoxicity of the genetically modified cell as compared to the mammalian cell without said genetic modification,
   (2) a reduction of in vitro peripheral blood mononuclear cell proliferation of the genetically modified cell as compared to the mammalian cell without said genetic modification, or
   (3) an increase in the size and weight of tumor formation by the genetically modified cell as compared to the mammalian cell without said genetic modification in humanized NOD scid gamma, NSG mice.

2. The method of claim 1, wherein the genetically modified mammalian cell expresses HLA-G protein for at least 20 weeks.

3. The method of claim 1, wherein the genetically modified mammalian cell expresses HLA-G protein for at least 50 weeks.

4. The method of claim 1, wherein the genetically modified mammalian cell expresses HLA-G protein on the cell surface of the genetically modified mammalian cell.

5. The method of claim 1, wherein the genetically modified mammalian cell is a human cell.

6. The method of claim 1, wherein the genetically modified cell is selected from the group consisting of a stem cell, a progenitor cell, a cell obtained by in vitro differentiation of the stem cell or the progenitor cell, a fully differentiated cell, an epidermal progenitor cell, a pancreatic progenitor cell, a hematopoietic stem cell, a keratinocyte, a fibroblast, a hepatocyte, a mesenchymal stem cell, a cardiomyocyte, a neural stem cell, a neuron, and an astrocyte.

7. The method of claim 1, wherein the genetically modified cell is selected from the group consisting of a human embryonic stem cell, a human mesenchymal stem cell, a human embryonic epidermal progenitor cell, and a human dermal fibroblast.

8. The method of claim 1, wherein the exogenous nucleic acid is an expression vector.

9. The method of claim 8, wherein the expression vector is a transposon vector.

10. The method of claim 8, wherein the expression vector further comprises a nucleic acid sequence encoding a reporter protein.

11. A method of producing an artificial tissue, a skin-graft, a skin-repair, or a skin-regeneration composition comprising the genetically modified mammalian cell produced by the method of claim 1.

12. The method of claim 1, wherein genetically modifying a mammalian cell with an exogenous nucleic acid comprises stably transfecting the mammalian cell with the exogenous nucleic acid.

13. The method of claim 1, wherein the genetically modified mammalian cells are selected using antibiotic resistance or flow cytometry.

* * * * *